(12) United States Patent
Hamed et al.

(10) Patent No.: US 9,474,721 B2
(45) Date of Patent: *Oct. 25, 2016

(54) ABUSE-RESISTANT FORMULATIONS

(71) Applicant: Cima Labs Inc., Brooklyn Park, MN (US)

(72) Inventors: Ehab Hamed, Concord, MA (US); Manuel A. Vega Zepeda, Minnetonka, MN (US)

(73) Assignee: Cima Labs Inc., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/296,572

(22) Filed: Jun. 5, 2014

(65) Prior Publication Data

US 2014/0294953 A1 Oct. 2, 2014

Related U.S. Application Data

(60) Division of application No. 13/470,963, filed on May 14, 2012, now abandoned, which is a continuation of application No. PCT/US2010/060755, filed on Dec. 16, 2010.

(60) Provisional application No. 61/287,515, filed on Dec. 17, 2009.

(51) Int. Cl.
| | | |
|---|---|---|
| *A61K 9/70* | (2006.01) | |
| *A61K 9/20* | (2006.01) | |
| *A61K 31/485* | (2006.01) | |
| *A61K 9/50* | (2006.01) | |

(52) U.S. Cl.
CPC .............. *A61K 9/70* (2013.01); *A61K 9/2054* (2013.01); *A61K 9/2081* (2013.01); *A61K 31/485* (2013.01); *A61K 9/5015* (2013.01); *A61K 9/5047* (2013.01)

(58) Field of Classification Search
CPC .... A61K 9/5015; A61K 9/5047; A61K 9/70; A61K 9/2081; A61K 9/2054; A61K 31/485
USPC ......... 424/464, 484, 485, 487, 488; 514/282
See application file for complete search history.

(56) References Cited

U.S. PATENT DOCUMENTS

| | | | |
|---|---|---|---|
| 4,990,341 A | 2/1991 | Goldie et al. | |
| 8,445,018 B2 * | 5/2013 | Habib et al. | 424/488 |
| 8,927,025 B2 * | 1/2015 | Hamed | 424/495 |
| 2002/0044966 A1 * | 4/2002 | Bartholomaeus et al. | 424/468 |
| 2003/0068375 A1 * | 4/2003 | Wright et al. | 424/468 |
| 2008/0069891 A1 * | 3/2008 | Habib et al. | 424/494 |

FOREIGN PATENT DOCUMENTS

| | | |
|---|---|---|
| EP | 1430897 | 6/2004 |
| EP | 2057984 | 5/2009 |
| WO | WO2006/002884 | 1/2006 |
| WO | WO2008/033523 | 3/2008 |
| WO | WO2009/035474 | 3/2009 |

OTHER PUBLICATIONS

International Search Report dated Jan. 25, 2012.

* cited by examiner

*Primary Examiner* — Blessing M Fubara

(57) ABSTRACT

The disclosure relates to a sustained-release oral dosage form for once-a-day administration comprising a matrix containing a viscosity modifier and coated granules containing hydromorphone. The dosage form can have a release profile such that 16 hours following administration, less than about 85 percent of the hydromorphone is released. In addition, the dosage form may have alcohol and/or crush resistance.

12 Claims, 8 Drawing Sheets

ABUSE-RESISTANT FORMULATIONS

CROSS REFERENCE TO RELATED APPLICATIONS

This application is a divisional of U.S. patent application Ser. No. 13/470,963, filed May 14, 2012, which is a continuation of PCT Patent Application No. PCT/US2010/060755, filed Dec. 16, 2010, now published as WO 2011/084593, publication date Jul. 14, 2011, which claims the benefit of U.S. Provisional Patent Application No. 61/287,515, filed Dec. 17, 2009, the disclosures of which are hereby incorporated herein by reference.

TECHNICAL FIELD

This invention relates to a sustained-release oral dosage form of hydromorphone for once-a-day administration.

BACKGROUND

Hydromorphone is administered to patients to reduce pain. Successful pain management in many of these patients requires maintenance of certain blood levels of hydromorphone throughout the day. One way of obtaining acceptable blood levels, used commonly in the pharmaceutical industry, is providing a dose which contains far more drug than is necessary to obtain the desired blood level. Blood levels shortly after the tablet is ingested reach a maximum or $C_{max}$ in a relatively short time, often within hours of ingestion ($T_{max}$) and thereafter, as the body uses, processes and excretes drug from the blood system, the blood level drops. If the $C_{max}$ attained is sufficiently high, and the body's clearance of the drug is sufficiently slow, the blood levels may not fall to sub-therapeutic levels for 4-12 hours or even longer. With drugs like hydromorphone, however, this is an impractical and inefficient dosing system. In addition, there is a risk to the patient in that such high initial API levels can cause significant side effects.

Another method of administering hydromorphone involves the use of an extended release mechanism. An extended release can be achieved in many different ways and there are many different release profiles that can be attained. Not only could this strategy reduce the number of doses that need to be taken in a day, it also may prevent one from being exposed to the side effects which can come from unnecessarily high initial blood levels.

Those who seek to abuse hydromorphone to "get high" can be frustrated by such extended and indeed other controlled release strategies. These strategies actively prevent one from obtaining high blood levels of the drug which can cause the euphoria or other physiologic effects which they are actually seeking, but which normal patients would consider an undesirable or even dangerous side effect. Such prescription drug abusers have learned to circumvent controlled release mechanisms by various administrative abuse means including simply chewing extended release tablets or crushing them using a mortar and a pestle for injection or the like. Another way to circumvent controlled release coatings is to attempt to dissolve the dosage form in a solvent such as water or ethanol. The latter can be particularly dangerous as hydromorphone should not be taken with alcohol. Depending upon the extended release formulation, the ethanol or water may act as a solvent, dissolving or eroding the dosage form and circumventing the intended controlled release. The resulting material can then be administered generally, orally, or in a syringe by a drug abuser.

Such abuse can have rather far ranging consequences. For example, cancer patients, patients with post-operative or pre-operative pain, and patients with chronic pains from arthritis or back injuries need to have useful drugs (e.g., hydromorphone) available to them. The potential for abuse, however, is a constant concern to regulators and law enforcement as these prescription drugs may be more freely obtainable than truly illegal illicit substances. There are also the societal problems relating to drug use, which includes the cost of their health care, the cost of their rehabilitation, the increase in crime which may come from supporting their drug habit, and the like.

SUMMARY

Sustained-release oral dosage forms for once-a-day administration of hydromorphone are provided. As described herein, dosages that are extended release, such as once-a-day, typically contain a larger concentration of pharmaceutically active ingredients. Such larger concentrations of pharmaceutically active ingredients make the dosage forms more dangerous, especially if the dosage forms are susceptible to dumping the pharmaceutically active ingredients (releasing an undesirable high concentration of the active ingredient in a short amount of time) when they are crushed, taken with alcohol, and/or are taken with food. Therefore, dosage forms that are resistant to one or more causes of dose dumping are desirable.

The dosage forms described herein can include a matrix having a viscosity modifier and coated granules comprising hydromorphone or a salt form thereof (e.g., hydromorphone HCl). In some cases, a dosage form, as described herein, has a release profile such that after 16 hours in 500 mL of 0.1N HCl, less than about 85 percent of the hydromorphone is released. In addition, a dosage form may have alcohol, crush resistance, and/or be resistant to food effect. Furthermore, a dosage form, as described herein, has a release profile which is not significantly affected by varying pH conditions, e.g. between low, acidic, pH and neutral pH. Dosage forms can be also resistant to food effect, meaning that the Cmax of the dosage form will not change more than 50%, 45%, 40%, or 35% when it is consumed with food vs. without food. One of ordinary skill in the art will appreciate that formulations that are resistant to food effect are generally safer, because their safety is not as reliant upon patient compliance.

Provided herein is a sustained-release oral dosage form for once-a-day administration comprising: a matrix, wherein the matrix comprises a viscosity modifier in an amount from about 20 to about 60 percent by weight of the dosage form; and coated granules comprising hydromorphone or a salt form thereof, such as hydromorphone hydrochloride. In some embodiments, the release of hydromorphone from the dosage form after 16 hours is less than about 85 percent. In some embodiments, the release of the hydromorphone from the dosage form after 20 hours is less than about 90 percent.

In some embodiments, the percent of hydromorphone released after 2 hours in a solution of 0.1N HCl and 40% alcohol is no more than 10 percentage points greater than the percent of hydromorphone released in a solution of 0.1N HCl in the absence of alcohol. In some embodiments, the release of hydromorphone from the dosage form 30 minutes after simulated oral tampering is less than about 50 percent.

In some embodiments, when the dosage form is administered to a group of at least five fasted healthy humans, at 2 hours following administration of the dosage form, the mean blood levels of hydromorphone in the humans are at least about 50 percent of the mean $C_{max}$, and the mean hydromorphone blood levels are maintained above at least about 50 percent of the mean $C_{max}$ for 24 hours following administration. In some embodiments, when the dosage form is administered to a group of at least five fasted healthy humans, at 2 hours following administration of the dosage form, the ratio of the mean $C_{max}$ to the mean plasma hydromorphone level is from about 1.0 to about 3.0, and at 24 hours the ratio of the mean $C_{max}$ to the mean plasma hydromorphone level is from about 1.0 to about 3.0. For example, the ratios at 2 hours and 24 hours can independently be from about 1.0 to less than about 2.0. In some embodiments, the median $T_{max}$ measured in the humans is from about 5 to about 15 hours, including from about 8 to about 15 hours.

In some embodiments, when the dosage form is administered to a group of at least five fasted healthy humans with and without co-ingestion of alcohol, the ratio of the mean $C_{max}$ after co-ingestion with alcohol to the mean $C_{max}$ without alcohol is from about 0.5 to about 1.8. The alcohol can be administered in amount of 4, 20 or 40 percent v/v alcohol in water.

A viscosity modifier can be selected from the group consisting of: sodium alginate, hydroxypropylmethylcellulose, hydroxyethylcellulose, hydroxypropylcellulose, methylcellulose, carboxymethylcellulose, sodium carboxymethylcellulose, polyvinylpyrrolidone, crosslinked polyacrylic acid, gelatin, pectins, gums, polyethylene oxides, Konjac flour, carrageenan, xanthan gum, or mixtures thereof. For example, a viscosity modifier can be a gelling polymer, such as natural and synthetic starches, natural and synthetic celluloses, acrylates, and polyalkylene oxides. In some embodiments, the gelling polymer is selected from the group consisting of: hydroxypropylmethylcellulose, hydroxypropylcellulose, methylcellulose, hydroxyethylcellulose, and carboxymethylcellulose. For example, in some cases a gelling polymer can be hydroxypropylmethylcellulose.

In some embodiments, the viscosity modifier is present in an amount from about 25 to about 45 percent by weight of the dosage form. For example, the viscosity modifier can be present in an amount from about 30 to about 40 percent by weight of the dosage form. In some embodiments, the viscosity modifier is present in an amount from about 33 to about 37 percent by weight of the dosage form. For example, the viscosity modifier is present in an amount of about 35 percent by weight of the dosage form.

A coated granule, as described herein, can comprise a granule comprising hydromorphone or a salt form thereof in an amount from about 0.1 to about 90 percent by weight of the granule, a first strong film former in an amount from about 1 to about 90 percent by weight of the granule, a second viscosity modifier in an amount from about 1 to about 90 percent by weight of the granule, and a first fat/wax in an amount from about 0 to about 40 percent by weight of the granule; and a coating on the granule, wherein the coating is present in an amount from about 20 to about 80 percent by weight of the coated granule, and wherein the coating comprises a second strong film former in an amount from about 10 to about 50 percent by weight of the coated granule, and a second fat/wax in an amount from about 10 to about 30 percent by weight of the coated granule.

The first and second strong film formers can be independently selected from the group consisting of: natural and synthetic starches, natural and synthetic celluloses, acrylics, vinylics, resins, methacrylate or shellac. For example, the first and second strong film formers can be independently selected from the group consisting of: ethylcellulose; Ammonio Methacrylate Copolymer, Type B; Ammonio Methacrylate Copolymer, Type A; Amino Methacrylate Copolymer; Ethyl Acrylate and Methyl Methacrylate Copolymer Dispersion; Methacrylic Acid Copolymer, Type A; Methacrylic Acid Copolymer, Type B; and shellac. In some embodiments, the first and second strong film formers are ethylcellulose. In some embodiments, the first strong film former and the second strong film former are the same.

In some embodiments, the first strong film former is present in an amount from about 10 to about 60 percent by weight of the granule. For example, the first strong film former can be present in an amount from about 15 to about 30 percent by weight of the granule.

The second viscosity modifier can be selected from the same group as defined above for the first viscosity modifier. For example, the second viscosity modifier can be selected from the group consisting of: sodium alginate, hydroxypropylmethylcellulose, hydroxyethylcellulose, hydroxypropylcellulose, methylcellulose, carboxymethylcellulose, sodium carboxymethylcellulose, polyvinylpyrrolidone, crosslinked polyacrylic acid, gelatin, pectins, gums, polyethylene oxides, Konjac flour, carrageenan, xanthan gum, or mixtures thereof. In some embodiments, the second viscosity modifier is selected from the group consisting of: hydroxypropylmethylcellulose, hydroxypropylcellulose, methylcellulose, hydroxyethylcellulose, and carboxymethylcellulose. For example, the second viscosity modifier can be hydroxypropylmethylcellulose.

In some embodiments, the second viscosity modifier is present in an amount from about 10 to about 70 percent by weight of the granule. For example, the second viscosity modifier can be present in an amount from about 25 to about 60 percent by weight of the granule.

The first and second fat/wax can be independently selected from the group consisting of: glycerol fatty esters, fatty glyceride derivatives, waxes, or fatty alcohols. For example, the first and second fat/wax can be independently selected from the group consisting of: glycerol behenate, glycerol palmitostearate, stearoyl macroglycerides, carnauba wax, bees wax, microcrystalline wax, and cetyl alcohol. In some embodiments, the first and second fat/wax are glycerol behenate. In some embodiments, the first fat/wax and the second fat/wax are the same.

In some embodiments, the second fat/wax is present in an amount from about 10 to about 25 percent by weight of the coated granule. In some embodiments, the granule does not contain a first fat/wax and the second fat/wax is present in an amount from about 10 to about 25 percent by weight of the coated granule.

In some embodiments, the hydromorphone salt is hydromorphone hydrochloride. In some embodiments, the hydromorphone or salt form thereof is present in an amount from about 1 to about 60 percent by weight of the granule. For example, the hydromorphone or salt form thereof is present in an amount from about 15 to about 40 percent by weight of the granule.

The granule can also comprise an antioxidant. Examples of antioxidants include butylated hydroxyanisole, ascorbic acid, glutathione, lipoic acid, uric acid, carotenes, α-tocopherol, selenium, resveratrol, tumeric, curcumin, ubiquinol, ascorbyl palmitate, butylated hydroxyl toluene, propyl gallate, citric acid, fumaric acid, malic acid, propionic acid, phosphoric acid, sodium sulfite, sodium thiosulfate, sodium bisulfite, sodium metabisulfite, potassium metabisulfite, methionine, erythorbic acid, ethyl oleate, sodium ascorbate, and mixtures thereof.

The granules are coated and in some embodiments, the coating is present in an amount from about 30 to about 70 percent by weight of the coated granule. For example, the coating can be present in an amount from about 40 to about 55 percent by weight of the coated granule.

In some embodiments, the coated granule comprises less than about 5 percent water per weight of the coated granule. For example, the coated granule comprises less than about 3 percent water per weight of the coated granule.

Also provided herein is sustained-release oral dosage form for once-a-day administration comprising: a matrix, wherein the matrix comprises a viscosity modifier in an amount from about 20 to about 60 percent by weight of the dosage form; and coated granules, wherein the coated granules comprise: a granule comprising hydromorphone or a salt form thereof in an amount from about 0.1 to about 90 percent by weight of the granule, a first strong film former in an amount from about 1 to about 90 percent by weight of the granule, a second viscosity modifier in an amount from about 1 to about 90 percent by weight of the granule, and a first fat/wax in an amount from about 0 to about 40 percent by weight of the granule; and a coating on the granule, wherein the coating is present in an amount from about 20 to about 80 percent by weight of the coated granule, and wherein the coating comprises a second strong film former in an amount from about 10 to about 50 percent by weight of the coated granule, and a second fat/wax in an amount from about 10 to about 25 percent by weight of the coated granule.

In some cases, the dosage form can comprise a matrix, wherein the matrix comprises hydroxypropylmethylcellulose in an amount from about 25 to about 45 percent by weight of the dosage form; and coated granules, wherein the coated granules comprise: a granule comprising hydromorphone in an amount from about 10 to about 60 percent by weight of the granule, ethylcellulose in an amount from about 10 to about 60 percent by weight of the granule, hydroxypropylmethylcellulose in an amount from about 10 to about 70 percent by weight of the granule, and glycerol behenate in an amount from about 0 to about 20 percent by weight of the granule; and a coating on the granule, wherein the coating is present in an amount from about 30 to about 70 percent by weight of the coated granule, and wherein the coating comprises ethylcellulose in an amount from about 20 to about 50 percent by weight of the coated granule, and glycerol behenate in an amount from about 10 to about 25 percent by weight of the coated granule.

Further provided herein is a dosage form comprising: a matrix, wherein the matrix comprises hydroxypropylmethylcellulose in an amount of about 35 percent by weight of the dosage form; and coated granules, wherein the coated granules comprise: a granule comprising hydromorphone in an amount of about 27 percent by weight of the granule, ethylcellulose in an amount from about 19 to about 21 percent by weight of the granule, and hydroxypropylmethylcellulose in an amount from about 51 to about 53 percent by weight of the granule; and a coating on the granule, wherein the coating is present in an amount of about 45 percent by weight of the coated granule, and wherein the coating comprises ethylcellulose in an amount from about 28 to about 32 percent by weight of the coated granule, and glycerol behenate in an amount from about 14 to about 16 percent by weight of the coated granule.

In some embodiments, the release of hydromorphone from a dosage form after 16 hours is less than about 85 percent. In some embodiments, the percent of hydromorphone released after 2 hours in a solution of 0.1N HCl and 40% alcohol is no more than 10 percentage points greater than the percent of hydromorphone released in a solution of 0.1N HCl in the absence of alcohol.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
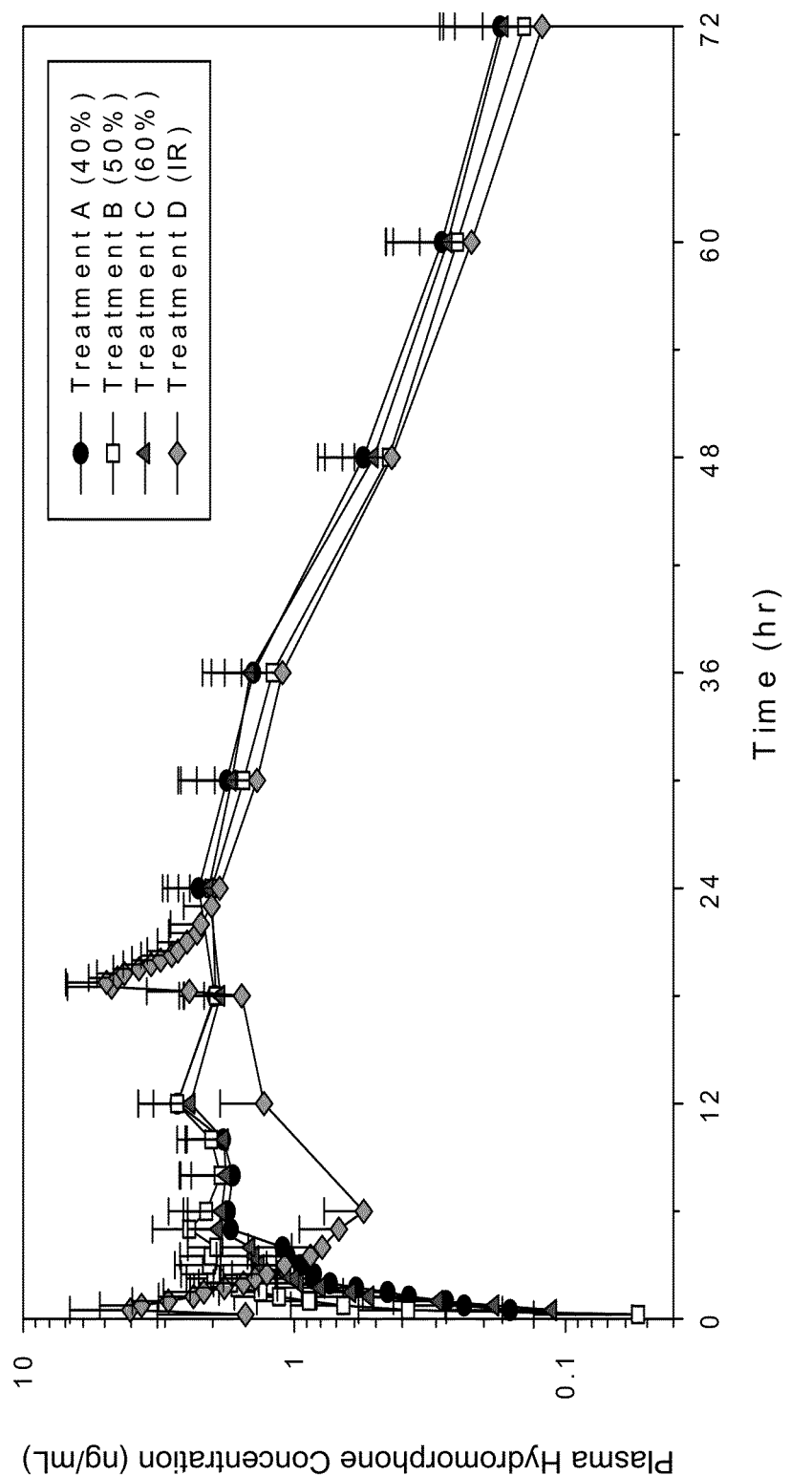
FIG. 1 is a line drawing of the plasma hydromorphone concentration as a function of time following administration of three sustained-release hydromorphone formulations to fasted healthy human subjects.
Figure 2:
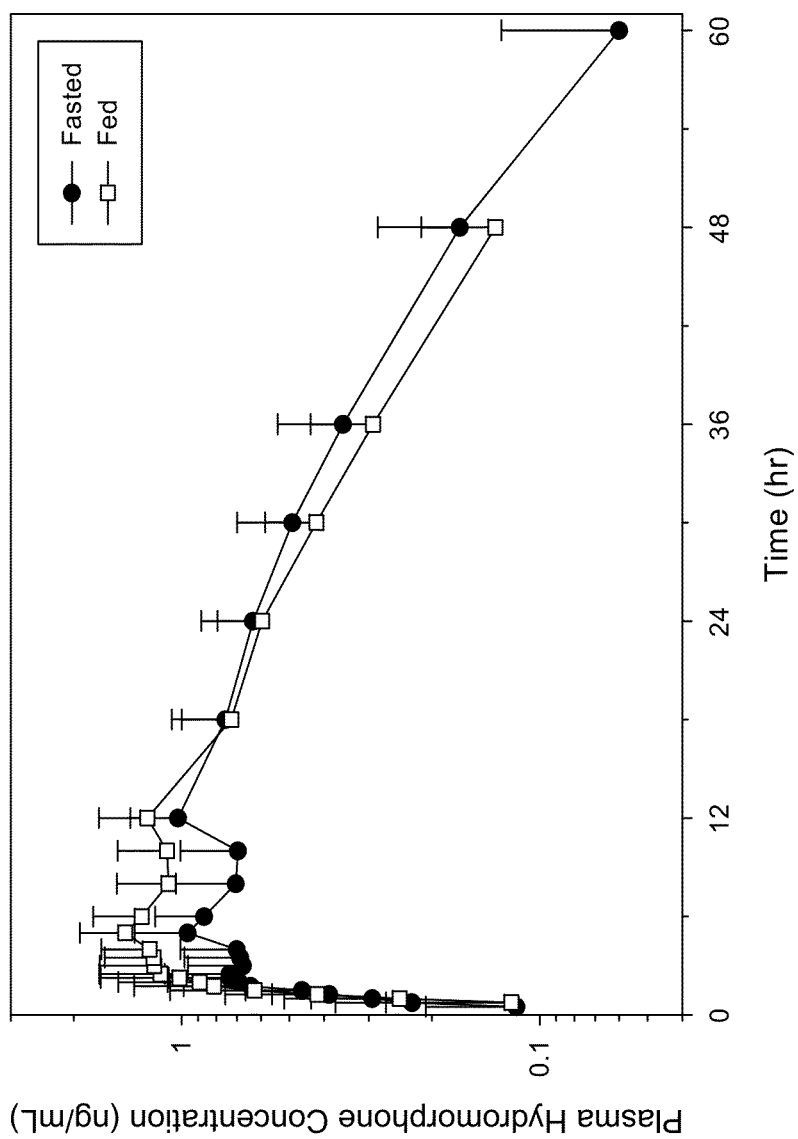
FIG. 2 is a line drawing of the plasma hydromorphone concentration as a function of time following administration of a sustained-release hydromorphone formulation in both fasted and fed healthy human subjects.
Figure 3:
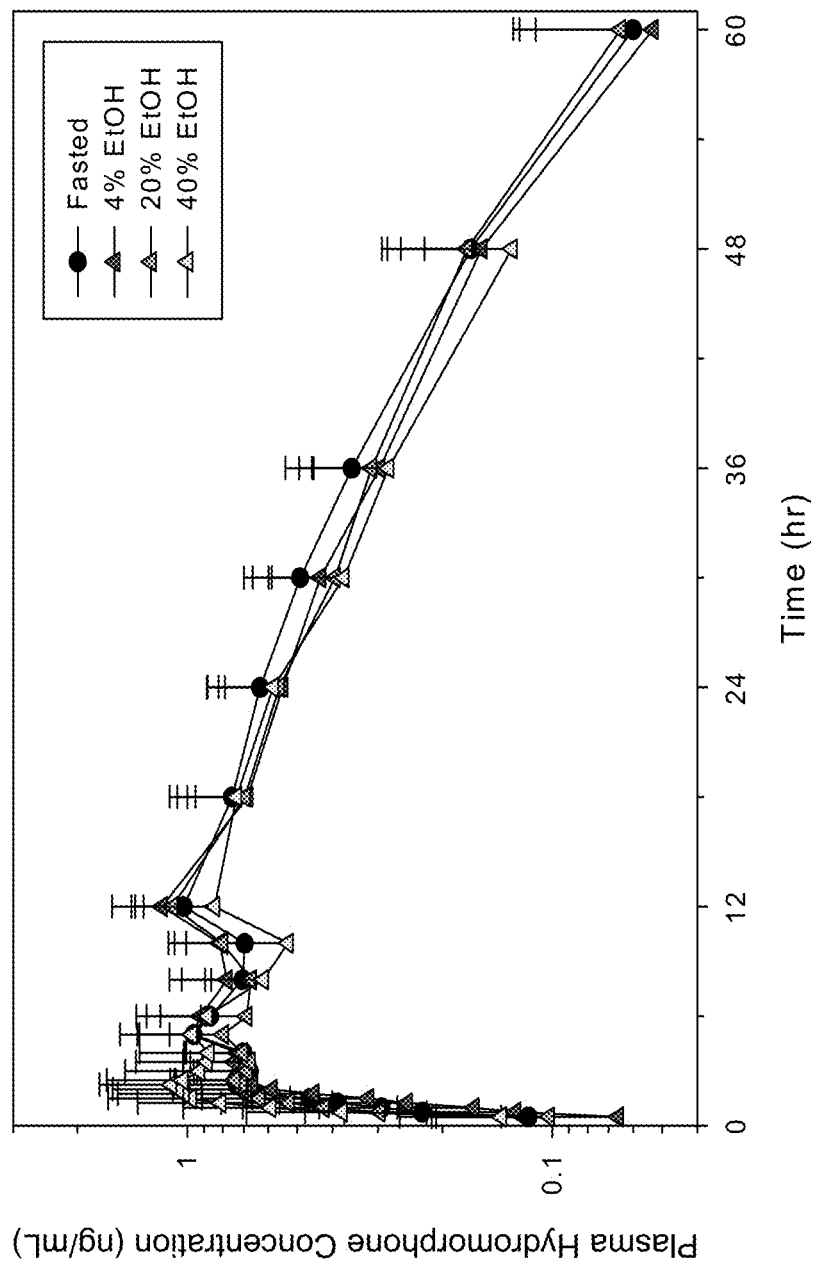
FIG. 3 is a line drawing of the plasma hydromorphone concentration as a function of time following administration of a sustained-release hydromorphone formulation co-administered with alcohol in fasted healthy human subjects.
Figure 4:
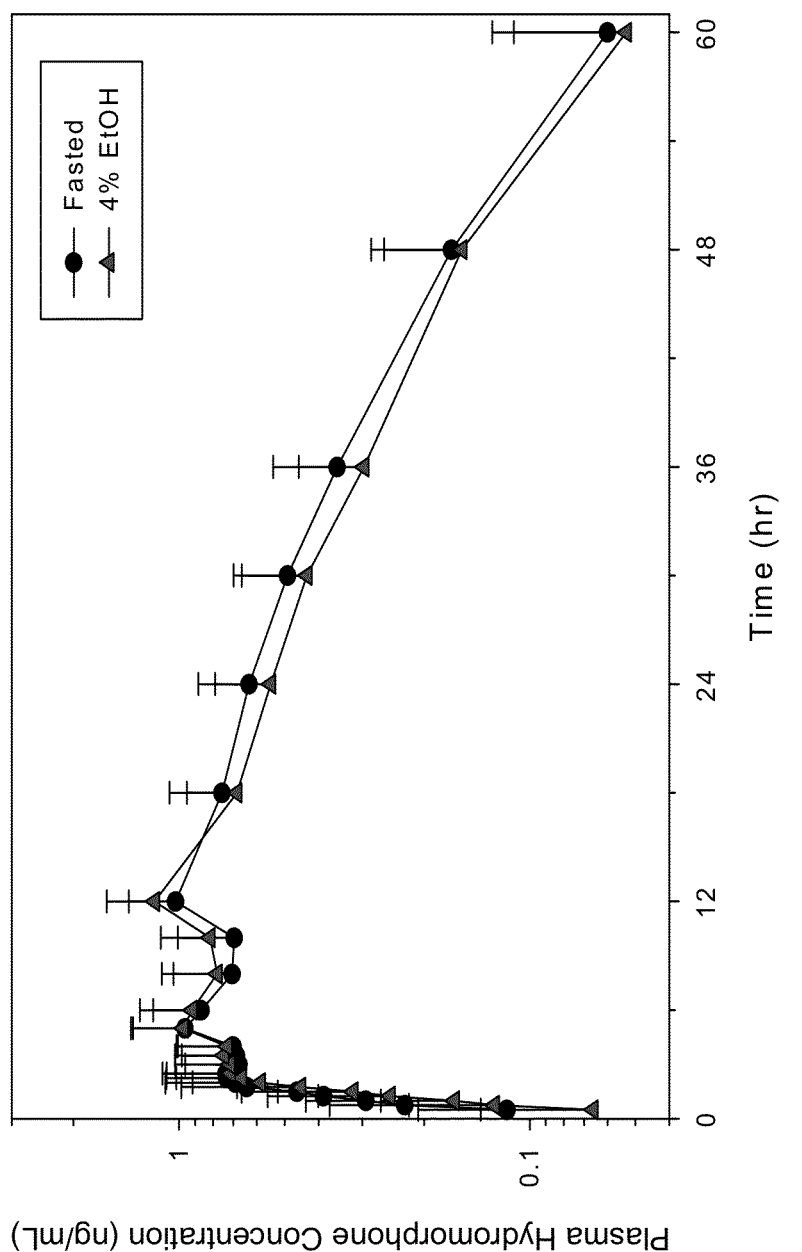
FIG. 4 is a line drawing comparing the plasma hydromorphone concentration as a function of time following administration of a sustained-release hydromorphone formulation co-administered with 4% ethanol in fasted healthy human subjects.
Figure 5:
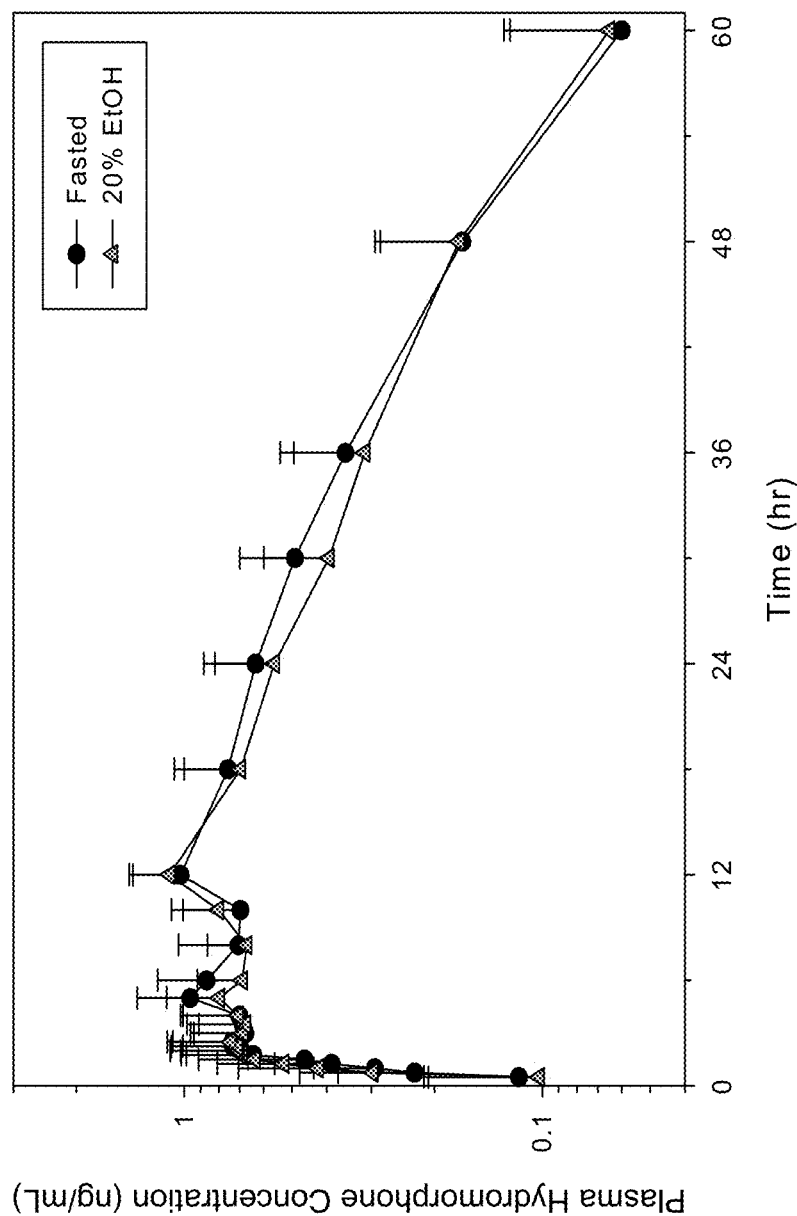
FIG. 5 is a line drawing comparing the plasma hydromorphone concentration as a function of time following administration of a sustained-release hydromorphone formulation co-administered with 20% ethanol in fasted healthy human subjects.
Figure 6:
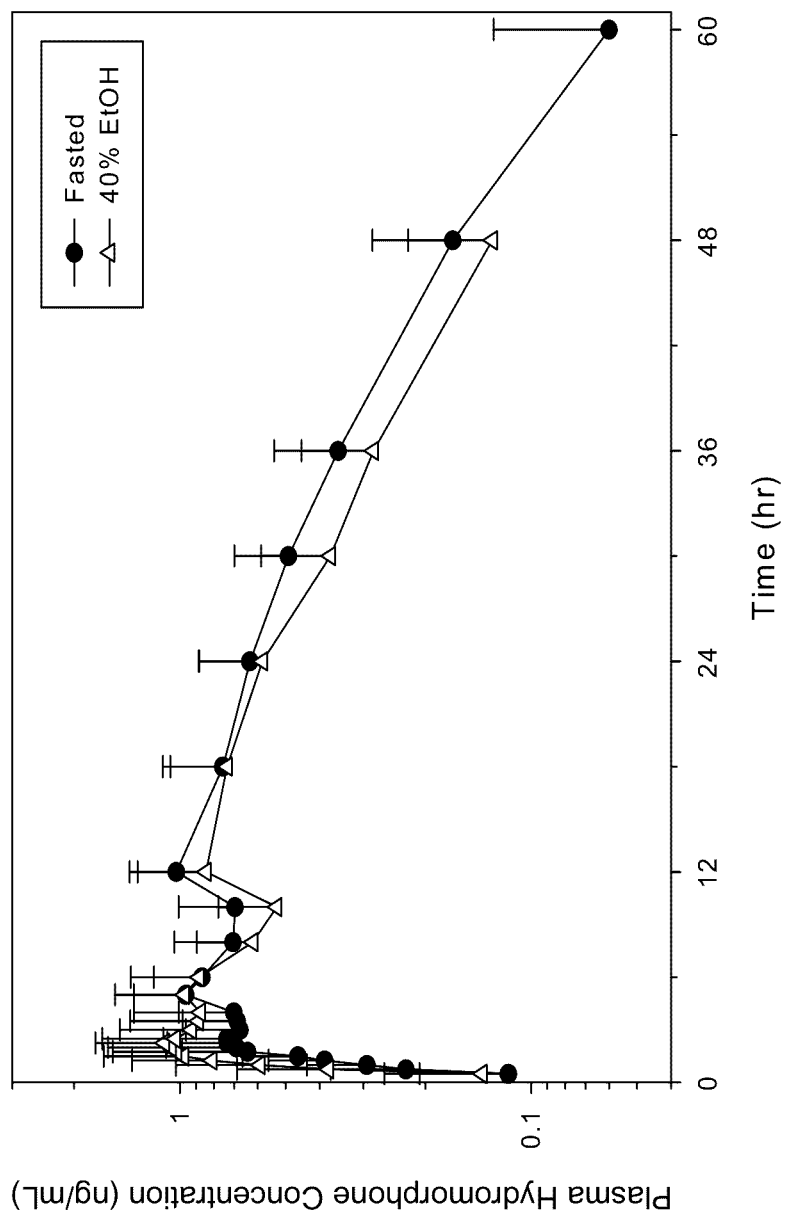
FIG. 6 is a line drawing comparing the plasma hydromorphone concentration as a function of time following administration of a sustained-release hydromorphone formulation co-administered with 40% ethanol in fasted healthy human subjects.

Sustained-release oral dosage forms for once-a-day administration of hydromorphone are provided. A dosage form can include a matrix having a viscosity modifier and coated granules comprising hydromorphone or a salt form thereof (e.g., hydromorphone HCl). In some cases, a dosage form, as described herein, has a release profile such that after 16 hours in 500 mL of 0.1N HCl, less than about 85 percent of the hydromorphone is released. In addition, a dosage form may have alcohol and/or crush resistance. Furthermore, a dosage form, as described herein, has a release profile which is not significantly affected by varying pH conditions, e.g. between low, acidic, pH and neutral pH.

The term "matrix" refers to a monolithic system comprising active substance-containing particles (e.g., coated granules) dispersed and entrapped in a continuum of excipients, i.e., the "matrix forming" substances; see, for example, Colombo, P., Santi, P., Siepmann, J., Colombo, G., Sonvico, F., Rossi, A., Luca Strusi, O., 2008. Swellable and Rigid Matrices Controlled Release Matrices with Cellulose Ethers.

In: Pharmaceutical Dosage Forms: Tablets, Volume 2: Rational Design and Formulation. Third Edition, Augsburger, L. and Hoag, S. (eds.). Informa Healthcare, New York, London. As set forth further herein, coated granules comprising hydromorphone are dispersed within a described matrix.

Provided herein is a sustained-release oral dosage form including a matrix, comprising a viscosity modifier in an amount from about 20 to about 60 percent (e.g., about 25 to about 60 percent, about 30 to about 60 percent, about 20 to about 55 percent, about 20 to about 50 percent, about 20 to about 45 percent, about 20 to about 40 percent, about 25 to about 45 percent, about 30 to about 40 percent, and about 33 to about 37 percent) by weight of the dosage form, and coated granules comprising hydromorphone or a salt form thereof. In some embodiments, the viscosity modifier is present in an amount from about 30 to about 60 percent by weight of the dosage form. In some embodiments, the viscosity modifier is present in an amount of about 35 percent by weight of the dosage form.

The dosage forms described herein can have a release profile such that the release of hydromorphone from the dosage form after 16 hours is less than about 85 percent. In some embodiments, the release of hydromorphone from the dosage form after 20 hours is less than about 90 percent. Release of hydromorphone is measured using the USP dissolution apparatus number 2 and 500 mL of a 0.1 N HCl solution as the dissolution medium. See Example 38.

Furthermore, the release of hydromorphone in 500 mL of a 0.1 HCl solution (pH about 1.2) as the dissolution medium is not significantly different from the release of hydromorphone in sodium acetate trihydrate buffer, adjusted to appropriate pH with glacial acetic acid (pH about 4.5) or in potassium phosphate monobasic buffer, adjusted to appropriate pH with 1 N sodium hydroxide (pH about 6.8). See FIGS. 7 and 8 and Example 41. The consistent release profiles at varying pH levels of formulations of the present invention is advantageous since it alleviates the effect of inter- and intra-patient variability in stomach and intestinal pH on the kinetics of drug release from the dosage form.

In some embodiments, the release of hydromorphone from the dosage form after administration to humans can also exhibit a fast rise and steady level of hydromorphone in the blood over a 24 hour period. For example, when tested in a group of at least five fasted healthy humans, the mean blood levels of hydromorphone can reach at least about 50% of the mean $C_{max}$ within 2 hours of administration of the dosage form and the mean hydromorphone blood levels can be maintained above at least about 50% of the mean $C_{max}$ for 24 hours following administration. In some cases, 2 hours following administration, the ratio of the mean $C_{max}$ to the mean plasma hydromorphone level is from about 1.0 to about 3.0. For example, the ratio can be from about 1.0 to less than about 2.0. 24 hours following administration, the ratio of the mean $C_{max}$ to the mean plasma hydromorphone level is from about 1.0 to about 3.0. For example, the ratio can be from about 1.0 to less than about 2.0. In another example, when tested in a group of at least five fasted healthy humans, the median $T_{max}$ is from about 5 to about 15 hours, including from about 8 to about 15 hours (e.g., about 8 to about 14 hours, about 8 to about 12 hours, about 8 to about 10 hours, about 9 to about 15 hours, about 10 to about 15 hours, about 12 to about 15 hours, about 13 to about 15 hours, and about 9 to about 12 hours). Release of hydromorphone following administration to human subjects can be measured using methods known to one of skill in the art. For example, concentrations of hydromorphone in human plasma samples can be measured using a validated high-performance liquid chromatography method with tandem mass spectrometric detection (LC-MS/MS).

The dosage form may be alcohol resistant. Resistance to alcohol is measured using the USP dissolution apparatus number 2 (paddles) at 37° C. and 500 mL of a 0.1 N HCl solution (normal dissolution) or a 0.1N HCl and 40% ethanolic solution (dose dumping dissolution) as the dissolution medium. For an alcohol resistant formulation, as described herein, after 2 hours in a solution of 0.1N HCl and 40% ethanol, the percent release of hydromorphone is no more than 10 percentage points greater than the percent of hydromorphone released in the 0.1N HCl solution in the absence of alcohol. For example, if the dosage form releases 20% of the hydromorphone in the 0.1N HCl solution in the absence of alcohol after 2 hours, then an alcohol resistant dosage form, as described herein, will not release any more than 30% of the hydromorphone in the solution having 0.1N HCl and 40% ethanol. See Example 38.

In some embodiments, when tested in a group of at least five fasted healthy humans with and without co-ingestion of a dosage form, as described herein, and alcohol (4, 20, and 40% v/v), the ratio of the mean $C_{max}$ after co-ingestion of alcohol to mean $C_{max}$ in the absence of alcohol is about 0.5 to about 1.8 (e.g., about 1.0 to about 1.8). Release of hydromorphone following administration to human subjects can be measured using methods known to one of skill in the art. For example, concentrations of hydromorphone in human plasma samples can be measured using a validated high-performance liquid chromatography method with tandem mass spectrometric detection (LC-MS/MS).

In some embodiments, a dosage form, as described herein, can be crush resistant. Crush resistance is measured using techniques designed to simulate oral tampering. Such methods involve placing a tablet of the dosage form in a ceramic mortar (13 cm outer diameter). A pestle is then used to apply force vertically downward onto the tablet until it breaks. The broken tablet is further crushed using a 360° circular motion with downward force applied throughout. The circular crushing motion is repeated eleven times (twelve strokes total). The resulting powder is transferred to a dissolution vessel to measure in vitro drug release. The in vitro release profile of the crushed tablet samples is obtained in 500 mL of 0.1N HCl dissolution medium. The samples are agitated at 50 rpm using USP apparatus 2 (paddles) at 37° C. After 30 minutes in the dissolution medium, a crush resistant dosage form exhibits a release of hydromorphone from the dosage form of less than about 50 percent. See Example 38.

The dosage form may be resistant to food effect. Resistance to food effect is measured using the methodology described in Example 41, provided herein. Generally, resistance to food effect is identified by comparing pharmacokinetic parameters from subjects that are fasted to those that have consumed a standard diet prior to administration. In some situations a standard diet can be high fat (i.e., about 50% of the calories are from fat), high carbohydrate or any other standard diet. A dosage form that is resistant to food effect (i.e., a % change in pharmacokinetic parameters comparing fasted and fed states) will show a smaller % change in pharmacokinetic parameters, such as $C_{max}$, $T_{max}$, or AUC at various time points when compared to other dosage forms. For example, the formulation described and tested in Example 41, below, showed a 0% change in $T_{max}$ between the fed and fasted data and the formulation tested in Example 40, below, showed an approximately 60% change in $T_{max}$ between the fed and fasted data. Thus, the formulation shown in Example 41 is more resistant to food effect. In some instances the percent change in $T_{max}$ will be less than 50%, 45%, 40%, 35%, 30%, 20%, 15% depending upon the formulation and its resistance to food effect.

In some embodiments, when tested in a group of at least five fasted healthy humans and compared to a group of at least 5 fed healthy humans, as described herein, the % change of the mean $C_{max}$ will be less than about 50%, 45%, 40%, 30%, 25%, 20%, or 15%. Similarly, the percent change in AUC at a specific time point can show less than a 50%, 45%, 40%, 35%, 30%, 20%, or 15% change when the fed and fasted data is compared. The concentration of hydromorphone human plasma samples can be measured using a validated high-performance liquid chromatography method with tandem mass spectrometric detection (LC-MS/MS).

The dosage forms described herein exhibit one or more of the above pharmokinetic and tamper-resistant characteristics.

A viscosity modifier, as described herein, is a material, which upon dissolution or dispersion in an aqueous solution or dispersion (e.g., water) at a concentration of 2% w/w (based on the dry material), creates a solution/dispersion with a viscosity of from about 100 to about 200,000 mPa·s (e.g., 4,000 to 175,000 mPa·s, and 75,000 to 140,000 mPa·s) as measured at 20° C. (±0.2° C.) using the analysis method described in the USP 33 monograph for hypromellose (incorporated herein by reference). Examples of viscosity modifiers include sodium alginate, hydroxypropylmethylcellulose, hydroxyethylcellulose, hydroxypropylcellulose, carboxymethylcellulose, sodium carboxymethylcellulose, methylcellulose, polyvinylpyrrolidone, crosslinked polyacrylic acid (e.g., carbomers), gelatin, pectins, gums (e.g., gum arabic, gum tragacanth, xanthan gums, and guar gums), polyethylene oxides, Konjac flour, carrageenan, or mixtures thereof. In some embodiments, the viscosity modifier is a natural or synthetic cellulose such as hydroxypropylmethylcellulose. In some embodiments, the viscosity modifier is a gelling polymer. Gelling polymers can include natural and synthetic starches, natural and synthetic celluloses, acrylates, and polyalkylene oxides. Examples include hydroxypropylmethylcellulose, hydroxypropylcellulose, methylcellulose, hydroxyethylcellulose, and carboxymethylcellulose. In some embodiments, the gelling polymer is hydroxypropylmethylcellulose (HPMC).

One or more viscosity modifiers can be used in the granules, coat on the granules, and in the matrix. As described herein, in some examples the matrix contains at least one viscosity modifier and less than 5%, 4%, 3%, 2%, or 1% of fat/wax. Such matrixes can show resistance to food effect.

When HPMC is used in the dosage form, the HPMC can have different methyl to hydroxypropyl substitution percent ratios ranging from 30:0 in the A-type, 29:8.5 for the E-type, 28:5 in the F-type, 22:8 for the K-type all available from DOW Chemical Company, Midland, Mich. or any other HPMC polymers available from other suppliers such as Aqualon.

Coated granules of the dosage forms described herein include a granule comprising hydromorphone or a salt form thereof and a coating on the granule. In some embodiments, a coated granule can include a granule comprising hydromorphone or a salt form thereof in an amount from about 0.1 to about 90 percent by weight of the granule, a first strong film former in an amount from about 1 to about 90 percent by weight of the granule, a second viscosity modifier in an amount from about 1 to about 90 percent by weight of the granule, and a first fat/wax in an amount from about 0 to about 40 percent by weight of the granule; and a coating on the granule, wherein the coating is present in an amount from about 20 to about 80 percent by weight of the coated granule, and wherein the coating comprises a second strong film former in an amount from about 10 to about 50 percent by weight of the coated granule, and a second fat/wax in an amount from about 0 to about 30 percent by weight of the coated granule.

Hydromorphone can be present in the dosage form as a neutral compound or as a salt form (e.g., hydromorphone hydrochloride). As used herein, references to hydromorphone include hydromorphone and salts thereof, especially hydromorphone hydrochloride. A person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002). In some embodiments, the hydromorphone or a salt form thereof is present in an amount from about 1 to about 60 percent by weight of the granule. In some embodiments, the hydromorphone or a salt form thereof is present in an amount from about 20 to about 50 percent by weight of the granule. In some embodiments, the hydromorphone or a salt form thereof is present in an amount from about 20 to about 35 percent by weight of the granule.

A strong film former is a polymer, which is at least slightly soluble, preferably, soluble in alcohol and at most slightly soluble in water and forms a dry 3-mil film with tensile strength not less than 1000 lb/in$^2$ when measured by the appropriate tensile strength measuring equipment such as the texture analyzer manufactured by Texture Technologies, Brookfield, Lloyd Instruments, and the like. For example, a strong film former can be selected from natural and synthetic starches, natural and synthetic celluloses, acrylics, vinylics and resins. In some embodiments, a strong film former is selected from ethylcellulose; polyvinyl acetate; (meth)acrylate copolymers such as Ammonio Methacrylate Copolymer, Type B (Eudragit RS); Ammonio Methacrylate Copolymer, Type A (Eudragit RL); Amino Methacrylate Copolymer (Eudragit E); Ethyl Acrylate and Methyl Methacrylate Copolymer Dispersion (Eudragit NE); Methacrylic Acid Copolymer, Type A (Eudragit L); Methacrylic Acid Copolymer, Type B (Eudragit S); and shellac. In some cases, the first and second strong film formers are the same.

In some embodiments, a strong film former is a natural or synthetic cellulose such as ethylcellulose (EC). Ethylcellulose is an inert, hydrophobic polymer and is essentially tasteless, odorless, colorless, non-caloric, and physiologically inert. There are many types of ethylcellulose which can be used, as long as they meet the other requirements, such as alcohol solubility, discussed herein. The ethylcellulose used can have different ethoxy content such as 48.0-49.5% described as N-type; 49.6-51.5% described as T-type; 50.5-52.5% described as X-type; all available from Aqualon, Hercules Research Center, Wilmington, Del.

The ethylcellulose used can have different molecular weights such as including EC polymers of the N-type that form 5% w/w solution in toluene:ethanol (80:20) that have viscosity ranges of 5.6-8.0 centipoise (cps) described as N7; 8.0-11 cps described as N10; 12-16 cps described as N14; 18-24 cps described as N22; 40-52 cps described as N50; 80-105 cps described as N100. The ethylcellulose used can also include different degrees of substitution of ethoxy groups per anhydroglucose unit, such as 2.65-2.81 for the X-type. N-type has values of 2.46-2.58.

In some embodiments, the first strong film former is present in an amount from about 10 to about 60 percent by weight of the granule. For example, the first strong film former can be present in an amount from about 15 to about 30 percent by weight of the granule. In some cases, the second strong film former is present in an amount from about 20 to about 50 percent by weight of the coated granule. For example, the second strong film former can be present in an amount from about 25 to about 40 percent by weight of the coated granule.

In some embodiments, a second viscosity modifier is the same as the viscosity modifier used in the matrix of the dosage form. In some cases, the second viscosity modifier is hydroxypropylmethylcellulose. In some embodiments, the second viscosity modifier is present in an amount from about 10 to about 70 percent by weight of the granule. In some embodiments, the second viscosity modifier is present in an amount from about 25 to about 60 percent by weight of the granule.

A fat/wax, as used herein, is generally hydrophobic and a solid at room temperature (25° C.). Fats are fatty acid based compounds generally having a hydrophilic/lipophilic balance (HLB) of about 6 or less (e.g., 4 or less; 2 or less), and also have a melting point of at least 30° C. (e.g., at least 40° C.; at least 50° C.). In one embodiment, the fat has an HLB of about 6 or less and a melting point of at least about 30° C. In another embodiment, it has an HLB of about 4 or less and a melting point of at least about 40° C. In another embodiment, the fat has an HLB of about 2 or less and a melting point of at least 50° C. Fats, including fatty acids and fatty esters, may be substituted or unsubstituted, saturated or unsaturated. In some cases, they have a chain length of at least about 14. Fatty esters may include fatty acid groups bound to alcohols, glycols, or glycerol. With regard to glyercols, the glycerols may be mono-, di-, and tri-fatty substituted glycerols, or mixtures thereof. Thixotropic fats/waxes can also be used.

Suitable fat ingredients include, without limitation, glycerol fatty esters, fatty glyceride derivatives, waxes and fatty alcohols such as, for example, glycerol behenate (COMPRITOL®), glycerol palmitostearate (PRECIROL®), stearoyl macroglycerides (GELUCIRE® 50/13). In some embodiments, the fat/wax is glycerol behenate.

Waxes are very complex and difficult to classify. See Kirk-Othmer, *Encyclopedia of Chemical Technology* (4th ed. 1998) Vol. 25 pp. 614-26, the text of which is incorporated by reference. They often meet the criteria described previously for fats (e.g., HLB of about 6 or less and melting point of at least about 30° C., HLB of about 4 or less and a melting point of at least about 40° C., HLB of about 2 or less and a melting point of at least 50° C.), but waxes that do not meet these criteria may also be used. Waxes include, without limitation, insect and animal waxes, vegetable waxes, mineral waxes, petroleum waxes, and synthetic waxes. For example, beeswax, carnauba wax, condelilla wax, montan wax, ouricury wax, rice-bran wax, jojoba wax, microcrystalline wax, cetyl ester wax, anionic emulsifying wax, nonionic emulsifying wax and paraffin wax. In one embodiment, the fat/wax is a fatty acid ester of glycerol. For example, the fatty acid ester of glycerol can be glycerol behenate.

Fat/waxes used in accordance with the present invention may be used in a molten form. It has been discovered, however, that even when used as a generally solid, non-molten form such as relatively small particles at room temperature, they can provide some, if not all of the advantages as molten materials. Any usable particle size which allows for proper formation of the granules or coating and which provides the desired properties may be used. In some embodiments, the first and second fat/wax are the same. In some cases, the first fat/wax may be present in an amount from about 0 to about 20 percent by weight of the granule.

In some embodiments, the second fat/wax is present in an amount from about 5 to about 30 percent by weight of the coated granule. For example, the second fat/wax can be present from about 10 to about 25 percent by weight of the coated granule. In some embodiments, the fat/wax may be present in the coating of the granule but not in the core of the granule.

In some embodiments, the granule further includes a stabilizing agent such as an antioxidant. An antioxidant can be selected from butylated hydroxyanisole, ascorbic acid, glutathione, lipoic acid, uric acid, carotenes, α-tocopherol, selenium, resveratrol, tumeric, curcumin, ubiquinol, ascorbyl palmitate, butylated hydroxyl toluene, propyl gallate, citric acid, fumaric acid, malic acid, propionic acid, phosphoric acid, sodium sulfite, sodium thiosulfate, sodium bisulfite, sodium metabisulfite, potassium metabisulfite, methionine, erythorbic acid, ethyl oleate, sodium ascorbate, and mixtures thereof. In some embodiments, the antioxidant is present in an amount from about 0.001 to about 1% by weight of the granule (e.g. about 0.005 to about 0.2 percent; about 0.01 to about 0.2 percent). In some embodiments, the antioxidant is present in an amount of about 0.05 percent by weight of the granule.

An antioxidant can contribute to the stability of the dosage form. In particular, the antioxidant can protect the dosage form from degradation due to oxidation. In some embodiments, use of an antioxidant in the dosage form is accompanied with removal of water from the manufacturing process. Accordingly, in some embodiments, the coated granule comprises less than about 5 percent water per weight of the coated granule. For example, the coated granule can have less than about 3 percent water per weight of the coated granule. In some cases, organic solvents may replace the water in the processing of the granules. For example, alcohol, such as ethanol, or acetone may be used.

The term "coating" is meant to encompass a material which substantially surrounds the granules and provides some additional function, such as, without limitation, taste masking, storage stability, reduced reactivity, controlled release, and/or abuse resistance. In some embodiments, the coating is present in an amount from about 30 to about 70 percent by weight of the coated granule. For example, the coating can be present in an amount of about 40 to about 60 percent by weight of the coated granule, including about 45 percent.

In some embodiments, the sustained-release oral dosage form for once-a-day administration described herein comprises a matrix, wherein the matrix comprises hydroxypropylmethylcellulose in an amount from about 20 to about 60 percent by weight of the dosage form, for example, from about 30 to about 60 percent by weight, including about 35 percent by weight, of the dosage form; and coated granules, wherein the coated granules comprise a granule comprising hydromorphone or a salt form thereof in an amount from about 10 to about 60 percent by weight of the granule, ethylcellulose in an amount from about 10 to about 60 percent by weight of the granule, hydroxypropylmethylcellulose in an amount from about 10 to about 70 percent by weight of the granule, and glycerol behenate in an amount from about 0 to about 20 percent by weight of the granule; and a coating on the granule, wherein the coating is present in an amount from about 30 to about 70 percent by weight of the coated granule, and wherein the coating comprises ethylcellulose in an amount from about 20 to about 50 percent by weight of the coated granule, and glycerol behenate in an amount from about 10 to about 25 percent by weight of the coated granule.

In another embodiments, a sustained-oral dosage form comprises a matrix, wherein the matrix comprises hydroxypropylmethylcellulose in an amount of about 35 percent by weight of the dosage form; and coated granules, wherein the coated granules comprise a granule comprising hydromorphone hydrochloride in an amount of about 27 percent by weight of the granule, ethylcellulose in an amount from about 19 to about 21 percent by weight of the granule, and hydroxypropylmethylcellulose in an amount from about 51 to about 53 percent by weight of the granule; and a coating on the granule, wherein the coating is present in an amount of about 40, 45, 50, or 60 percent by weight of the coated granule, and wherein the coating comprises ethylcellulose in an amount from about 28 to about 32 percent by weight of the coated granule, and glycerol behenate in an amount from about 10 to about 20 percent by weight of the coated granule, including about 14 to about 16 percent by weight of the coated granule The coated granules and dosage forms as described herein can be prepared using methods known to those in the art, see, for example, U.S. Publication No. 2008/0311205, incorporated herein by reference. In general, hydromorphone or a salt form thereof is formulated into polymer-rich granules onto which a polymeric coat is applied. The coated granules are subsequently mixed with a viscosity modifier.

In some embodiments, the dosage form may also include at least one other ingredient or excipient in addition to the coated particle and viscosity modifier in the matrix. The other ingredient or excipient may include, but is not limited to, taste masking agents, binders, fillers, sugars, artificial sweeteners, polymers, flavoring agents, coloring agents, lubricants, glidants, bio- or muco-adhesives, surfactants, buffers, and disintegrants. The amount of any one or more of these ingredients will vary with the amount of coating, granule size, shape of the dosage form, form of the dosage form, number of ingredients used, the particular mixture of ingredients used, the number of dosage forms that will formulate a dose, the amount of hydromorphone per dose and the like. Any combination or amounts are contemplated sufficient to produce a dosage form having the described release profile and/or tamper-resistance provided.

"Taste masking agent(s)" include anything known to be used as a taste masking agents in this art. Examples include Eudragit E-100, ethylcellulose, hydroxypropylmethylcellulose, hydroxypropyl cellulose, methylcellulose, Hydroxyethylcellulose, carboxymethylcellulose, shellac, zein, carbomers, fats, waxes, glycerol mono-, di-, tri-glycerides, compritol, precirol, gelucires, poloxamers, modified chitosans, carrageenans, cellulose acetate trimellitate, hydroxypropyl methylcellulose phthalate, hydroxypropylmethylcellulose acetate succinate, methacrylic acid copolymers including Eudragit L 100, S 100, L30D-55, polyvinylacetate phthalate (PVAP). Taste masking agents can be used in conventional amounts, for example, in an amount of about 0 to about 50 percent by weight of the total dosage form (e.g., about 5 to about 40 percent by weight of the total dosage form; about 10 to about 30 percent by weight of the total dosage form).

Binders can be used to add cohesiveness to powders and provide the necessary bonding to form granules that can be compressed into hard tablets that have acceptable mechanical strength to withstand subsequent processing or shipping and handling. Examples of binders include acacia, tragacanth, gelatin, starch (both modified or unmodified), cellulose materials such as methylcellulose, ethylcellulose, hydroxypropylmethylcellulose, hydroxypropyl cellulose, hydroxyethylcellulose and sodium carboxy methylcellulose, alginic acids and salts thereof, magnesium aluminum silicate, polyethylene glycol, guar gum, polysaccharide acids, bentonites, sugars, invert sugars, and the like, fats, waxes, polyvinylpyrrolidone, polymethacrylate and other acrylic and vinyl-based polymers. Binders can be used in conventional amounts, for example, in an amount of about 0 to about 50 percent by weight of the total dosage form (e.g., about 2 to about 10 percent by weight of the total dosage form).

Fillers can include mannitol, dextrose, sorbitol, lactose, sucrose, and calcium carbonate. Fillers can be used in conventional amounts, for example, in an amount of about 0 to about 90 percent by weight of the total dosage form (e.g., from about 10 to about 50 percent by weight of the total dosage form). In some embodiments, a filler can be a sugar. For example, sugar, sugar alcohols, ketoses, saccharides, polysaccharides, oligosaccharides and the like, as well as celluloses and modified celluloses.

Sugars may also include direct compression and/or non-direct compression sugars. Non-direct compression sugars include, without limitation, dextrose, mannitol, sorbitol, trehalose, lactose and sucrose. These sugars generally exist as either a direct compression sugar, i.e., a sugar which has been modified to increase its compressibility and/or flow, or a non-direct compression sugar which does not have sufficient flowability and/or compressibility to allow it to be used in high speed processing and multi-tablet presses without some sort of augmentation such as, without limitation, a glidant to increase flow, granulation to increase flow and/or compressibility and the like. While not definitive, sometimes a non-direct compression sugar will have at least about 90% of its particles smaller than about 200 microns, and more preferably 80% smaller than about 150 microns.

The amount of total sugar can range from about 0 to about 90 (e.g., about 5 to about 75; about 10 and 50) by weight of the total dosage form. Other non-carbohydrate diluents and fillers which may be used include, for example, dihydrated or anhydrous dibasic calcium phosphate, tricalcium phosphate, calcium carbonate, anhydrous or hydrated calcium sulphate, and calcium lactate trihydrate. Non-carbohydrate diluents and fillers may be used in an amount of from about 0 to about 90 percent (e.g., from about 5 to about 75 percent; from about 10 to about 50 percent) by weight of the total dosage form.

Artificial sweeteners can include saccharin, aspartame, sucralose, neotame, and acesulfame potassium. Artificial sweeteners may be used in conventional amounts, for example, in an amount ranging from about 0.1 to about 2 percent by weight of the total dosage form.

Flavoring agents can include synthetic flavor oils and flavoring aromatics and/or natural oils, extracts from plants, leaves, flowers, fruits and so forth and combinations thereof. For example, cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavoring agents are vanilla, citrus oil, including lemon, orange, banana, grape, lime and grapefruit, and fruit essences, including apple, pear, peach, strawberry, raspberry, cherry, plum, pineapple, apricot and so forth.

Flavoring agents may be used in conventional amounts, for example, in an amount ranging from about 0.01 to about 3 percent by weight of the dosage form (e.g., from about 0.1 to about 2.5 percent by weight of the dosage form; from about 0.25 to about 2 percent by weight of the dosage form).

Coloring agents can include titanium dioxide, iron oxides such as red or yellow iron oxide, and dyes suitable for food such as those known as FD&C dyes and natural coloring agents such as grape skin extract, beet red powder, beta-carotene, annatto, carmine, turmeric, and paprika. Coloring agents may be used in conventional amounts, for example, in an amount ranging from about 0.001 to about 1% by weight of the total dosage form.

Lubricants can include intrinsic or extrinsic lubricants. Intrinsic lubricants may include magnesium, calcium, zinc salts of stearic acid, hydrogenated and partially hydrogenated vegetable oils, animal fats, polyethylene glycol, polyoxyethylene monostearate, talc, light mineral oils, magnesium oxide and the like. Lubricants may be used in conventional amounts, for example, in an amount from about 0.1 to about 5 percent by weight of the dosage form (e.g., from about 0.25 to about 2.5 percent; from about 0.5 to about 2 percent).

Surfactants can include, without limitation, various grades of the following commercial products: Arlacel®, Tween®, Capmul®, Centrophase®, Cremophor®, Labrafac®, Labrafil®, Labrasol®, Myverol®, Tagat®, and any non-toxic short and medium chain alcohols. Surfactants can be used in conventional amounts, for example, in an amount of about 0.01 to about 5 percent by weight of the dosage form (e.g., in an amount of about 0.1 to about 2 percent).

Buffers can include any weak acid or weak base or, preferably, any buffer system that is not harmful to the gastrointestinal mucosa. These include, but are not limited to, sodium carbonate, potassium carbonate, potassium carbonate, disodium hydrogen phosphate, sodium dihydrogen phosphate, and the equivalent potassium salts. Buffers can be used in conventional amounts, for example, in an amount of about 0.1 to about 10 percent by weight of the dosage form (e.g., from about 1 to about 5 percent).

The dosage form may also contain minor amounts of nontoxic substances such as wetting or emulsifying agents, pH buffering agents and the like, for example, sodium acetate, sorbitan monolaurate, triethanolamine, sodium acetate, triethanolamine oleate, sodium lauryl sulfate, dioctyl sodium sulfosuccinate, polyoxyethylene sorbitan fatty acid esters.

A "dosage form", as used herein, is a tablet, capsule, caplet, sachet, powder or other solid known for the administration of medicines orally. It is generally made from a mixture as defined herein and is generally formed (as in a tablet) into a form for use by a doctor or patient for administration.

Dosage forms may be provided in a range of shapes and sizes. In some embodiments, the dosage form is in a size capable of oral administration and provides a therapeutic amount of hydromorphone. Generally, such dosage forms will be less than 1.5 inches in any one direction, more preferably less than 1 inch and most preferably less than 0.75 inch. Shapes include but not limited to round with both flat or convex face, capsule shape (caplets), diamond shape, triangular, rectangular, hexagonal, pentagonal, heart-shaped, animal shaped tablets like rabbits, elephants etc. Dosage forms can be any size and shape, but preferable of a size and shape to avoid crushing or abuse.

Dosage forms are formulated for once-a-day administration. The amount of hydromorphone present in the dosage form can vary from about 2 mg to about 70 mg (e.g. 2 mg, 4 mg, 8 mg, 12 mg, 16 mg, 24 mg, 32 mg, and 64 mg). The dosage form may be used to manage persistent, moderate-to-severe pain in patients requiring continuous, around-the-clock pain relief for an extended period of time.

In some embodiments, the tablet can have a hardness from about 20-300 Newtons.

Tablets can either be manufactured by direct compression, wet granulation, dry granulation followed by coating and tablet compression or any other tablet manufacturing technique. See, e.g., U.S. Pat. Nos. 5,178,878, 5,223,264 and 6,024,981 which are incorporated by reference herein.

EXAMPLES

Example 1

32 mg Hydromorphone Formulation

TABLE 1

| Material | % w/w |
|---|---|
| Uncoated Granules | |
| hydromorphone HCl | 46.60 |
| hydroxypropylmethylcellulose (K100M) | 26.40 |
| ethylcellulose | 17.00 |
| Compritol (glycerol behenate) | 10.00 |
| Coated Granules | |
| uncoated granules | 50.00 |
| ethylcellulose | 33.33 |
| Compritol (glycerol behenate) | 16.67 |
| Dosage Form | |
| coated granules | 35.04 |
| lactose monohydrate | 44.46 |
| hydroxypropylmethylcellulose (K100M) | 20.00 |
| magnesium stearate | 0.50 |

Granules were manufactured in a high shear granulator where hydromorphone HCl, hydroxypropylmethylcellulose, compritol, and a portion of the ethylcellulose were dry mixed for 2 minutes. Then, a 10% hydro-ethanolic (30:70) solution of the remaining ethylcellulose was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 82 N.

Example 2

32 mg Hydromorphone Formulation

TABLE 2

| Material | % w/w |
|---|---|
| Uncoated Granules | |
| hydromorphone HCl | 46.60 |
| hydroxypropylmethylcellulose (K100M) | 36.40 |
| ethylcellulose | 17.00 |
| Coated Granules | |
| uncoated granules | 50.00 |
| ethylcellulose | 33.33 |
| Compritol (glycerol behenate) | 16.67 |
| Dosage Form | |
| coated granules | 34.33 |
| lactose monohydrate | 45.17 |
| hydroxypropylmethylcellulose (K100M) | 20.00 |
| magnesium stearate | 0.50 |

Granules were manufactured in a high shear granulator where hydromorphone HCl, hydroxypropylmethylcellulose, compritol, and a portion of the ethylcellulose were dry mixed for 2 minutes. Then, a 10% hydro-ethanolic (30:70) solution of the remaining ethylcellulose was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 88 N.

Example 3

32 mg Hydromorphone Formulation

TABLE 3

| Material | % w/w |
|---|---|
| Uncoated Granules | |
| hydromorphone HCl | 46.60 |
| hydroxypropylmethylcellulose (K100M) | 36.40 |

TABLE 3-continued

| Material | % w/w |
|---|---|
| ethylcellulose | 17.00 |
| Coated Granules | |
| uncoated granules | 50.00 |
| ethylcellulose | 33.33 |
| Compritol (glycerol behenate) | 16.67 |
| Dosage Form | |
| coated granules | 34.33 |
| lactose monohydrate | 45.17 |
| hydroxypropylmethylcellulose (K100M) | 20.00 |
| magnesium stearate | 0.50 |

Granules were manufactured in a high shear granulator where hydromorphone HCl, hydroxypropylmethylcellulose, compritol, and a portion of the ethylcellulose were dry mixed for 2 minutes. Then, a 10% hydro-ethanolic (30:70) solution of the remaining ethylcellulose was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 66 N.

Example 4

32 mg Hydromorphone Formulation

TABLE 4

| Material | % w/w |
|---|---|
| Uncoated Granules | |
| hydromorphone HCl | 26.90 |
| hydroxypropylmethylcellulose (K100M) | 50.30 |
| ethylcellulose | 22.80 |
| Coated Granules | |
| uncoated granules | 50.00 |
| ethylcellulose | 33.33 |
| magnesium stearate | 16.67 |
| Dosage Form | |
| coated granules | 64.52 |
| lactose monohydrate | 14.98 |
| hydroxypropylmethylcellulose (K100M) | 20.00 |
| magnesium stearate | 0.50 |

Granules were manufactured in a high shear granulator where hydromorphone HCl, hydroxypropylmethylcellulose, compritol, and a portion of the ethylcellulose were dry mixed for 2 minutes. Then, a 10% hydro-ethanolic (30:70) solution of the remaining ethylcellulose was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/magnesium stearate mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 36 N.

Example 5

32 mg Hydromorphone Formulation

TABLE 5

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| α-tocopherol | 0.05 |
| Coated Granules | |
| uncoated granules | 50.00 |
| ethylcellulose | 33.33 |
| Compritol (glycerol behenate) | 16.67 |
| Dosage Form | |
| coated granules | 58.39 |
| lactose monohydrate | 21.11 |
| hydroxypropylmethylcellulose (K100M) | 20.00 |
| magnesium stearate | 0.50 |

Granules were manufactured in a high shear granulator where hydromorphone HCl, hydroxypropylmethylcellulose and a portion of the ethylcellulose and were dry mixed for 2 minutes. Then, an ethanolic solution of the remaining ethylcellulose and α-tocopherol was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 58 N.

Example 6

32 mg Hydromorphone Formulation

TABLE 6

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 60.61 |
| lactose monohydrate | 18.89 |
| hydroxypropylmethylcellulose (K100M) | 20.00 |
| magnesium stearate | 0.50 |

Granules were manufactured in a high shear granulator where hydromorphone HCl, hydroxypropylmethylcellulose and a portion of the ethylcellulose and were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 62 N.

Example 7

12 mg Hydromorphone Formulation

TABLE 7

| Material | % w/w |
|---|---|
| Uncoated Granules | |
| hydromorphone HCl | 27.00 |
| hydroxypropylmethylcellulose (K100M) | 52.28 |

TABLE 7-continued

| Material | % w/w |
|---|---|
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 22.90 |
| lactose monohydrate | 16.60 |
| hydroxypropylmethylcellulose (K100M) | 60.00 |
| magnesium stearate | 0.50 |

Granules were manufactured in a high shear granulator where hydromorphone HCl, hydroxypropylmethylcellulose and a portion of the ethylcellulose and were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ⅜ inch round tablets weighed 400 mg and had an average hardness of 152 N.

Example 8

32 mg Hydromorphone Formulation

TABLE 8

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 40.71 |
| lactose monohydrate | 8.79 |
| hydroxypropylmethylcellulose (K100M) | 50.00 |
| magnesium stearate | 0.50 |

Granules were manufactured in a high shear granulator where hydromorphone HCl, hydroxypropylmethylcellulose and a portion of the ethylcellulose and were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The ½ inch round tablets weighed 600 mg and had an average hardness of 97 N.

Example 9

32 mg Hydromorphone Formulation

TABLE 9

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 45.00 |
| ethylcellulose | 36.67 |
| Compritol (glycerol behenate) | 18.33 |
| Dosage Form | |
| coated granules | 44.08 |
| lactose monohydrate | 20.42 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose and were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 55% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content.

The blended mixture was then compressed in a rotary tablet press to form tablets. The capsule-shaped tablets (0.625× 0.275 in) weighed 600 mg and had an average hardness of 138 N.

Example 10

32 mg Hydromorphone Formulation

TABLE 10

| Material | % w/w |
|---|---|
| Uncoated Granules | |
| hydromorphone HCl | 27.00 |
| hydroxypropylmethylcellulose (K100M) | 20.00 |
| ethylcellulose | 42.95 |
| Compritol (glycerol behenate) | 10.00 |
| butylated hydroxyanisole | 0.05 |
| Coated Granules | |
| uncoated granules | 45.00 |
| ethylcellulose | 36.67 |
| Compritol (glycerol behenate) | 18.33 |
| Dosage Form | |
| coated granules | 54.70 |
| lactose monohydrate | 9.80 |
| hydroxypropylmethylcellulose (K100M) | 35.00 |
| magnesium stearate | 0.50 |

Granules were manufactured in a high shear granulator where hydromorphone HCl, hydroxypropylmethylcellulose, compritol, and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 55% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 500 mg and had an average hardness of 56 N.

Example 11

12 mg Hydromorphone Formulation

TABLE 11

| Material | % w/w |
|---|---|
| Uncoated Granules | |
| hydromorphone HCl | 27.00 |
| hydroxypropylmethylcellulose (K100M) | 20.00 |
| ethylcellulose | 42.95 |

TABLE 11-continued

| Material | % w/w |
|---|---|
| Compritol (glycerol behenate) | 10.00 |
| butylated hydroxyanisole | 0.05 |
| Coated Granules | |
| uncoated granules | 45.00 |
| ethylcellulose | 36.67 |
| Compritol (glycerol behenate) | 18.33 |
| Dosage Form | |
| coated granules | 54.7 |
| lactose monohydrate | 9.80 |
| hydroxypropylmethylcellulose (K100M) | 35.00 |
| magnesium stearate | 0.50 |

Granules were manufactured in a high shear granulator where hydromorphone HCl, hydroxypropylmethylcellulose, compritol, and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 55% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The $5/16$ inch round tablets weighed 187.5 mg and had an average hardness of 23 N.

Example 12

12 mg Hydromorphone Formulation

TABLE 12

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 15.27 |
| lactose monohydrate | 36.73 |
| hydroxypropylmethylcellulose (K100M) | 47.50 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 241 N.

Example 13

12 mg Hydromorphone Formulation

TABLE 13

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 15.27 |
| lactose monohydrate | 24.23 |
| hydroxypropylmethylcellulose (K100M) | 60.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 239 N.

Example 14

12 mg Hydromorphone Formulation

TABLE 14

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 15.27 |
| lactose monohydrate | 24.23 |
| Celpheres CP-203 | 25.00 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose, hydroxypropylmethylcellulose, and Celpheres CP-203 in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 156 N.

Example 15

32 mg Hydromorphone Formulation

TABLE 15

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 37.56 |
| lactose monohydrate | 27.02 |
| hydroxypropylmethylcellulose (K100M) | 34.92 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 48 N.

Example 16

12 mg Hydromorphone Formulation

TABLE 16

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |

TABLE 16-continued

| Materials | % w/w |
|---|---|
| Coated Granules | |
| uncoated granules | 50.00 |
| ethylcellulose | 33.33 |
| Compritol (glycerol behenate) | 16.67 |
| Dosage Form | |
| coated granules | 14.08 |
| lactose monohydrate | 25.31 |
| Microcrystalline cellulose (Avicel PH 113) | 25.00 |
| hydroxypropylmethylcellulose (K100M) | 35.01 |
| Color | 0.10 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. The color and Avicel PH 113 were blended in a V-blender for 15 minutes and milled. The milled blend was blended with coated granules, lactose and hydroxypropylmethylcellulose for 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 154 N.

Example 17

32 mg Hydromorphone Formulation

TABLE 17

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 55.00 |
| ethylcellulose | 30.00 |
| Compritol (glycerol behenate) | 15.00 |
| Dosage Form | |
| coated granules | 38.36 |
| lactose monohydrate | 26.10 |

TABLE 17-continued

| Materials | % w/w |
|---|---|
| hydroxypropylmethylcellulose (K100M) | 35.06 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 45% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.5000×0.3125 in) weighed 600 mg and had an average hardness of 61 N.

Example 18

12 mg Hydromorphone Formulation

TABLE 18

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 22.90 |
| lactose monohydrate | 36.60 |
| hydroxypropylmethylcellulose (K100M) | 40.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The ⅜ inch round tablets weighed 400 mg and had an average hardness of 128 N.

Example 19

12 mg Hydromorphone Formulation

TABLE 19

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 22.90 |
| lactose monohydrate | 26.60 |
| hydroxypropylmethylcellulose (K100M) | 50.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The ⅜ inch round tablets weighed 400 mg and had an average hardness of 143 N.

Example 20

32 mg Hydromorphone Formulation

TABLE 20

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 61.07 |
| lactose monohydrate | 8.43 |
| hydroxypropylmethylcellulose (K100M) | 30.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The ⅜ inch round tablets weighed 400 mg and had an average hardness of 89 N.

Example 21

32 mg Hydromorphone Formulation

TABLE 21

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 40.71 |
| lactose monohydrate | 28.79 |
| hydroxypropylmethylcellulose (K100M) | 30.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The ½ inch round tablets weighed 600 mg and had an average hardness of 80 N.

Example 22

32 mg Hydromorphone Formulation

TABLE 22

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |

TABLE 22-continued

| Materials | % w/w |
|---|---|
| Coated Granules | |
| uncoated granules | 50.00 |
| ethylcellulose | 33.33 |
| Compritol (glycerol behenate) | 16.67 |
| Dosage Form | |
| coated granules | 40.71 |
| lactose monohydrate | 18.79 |
| hydroxypropylmethylcellulose (K100M) | 40.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The ½ inch round tablets weighed 600 mg and had an average hardness of 92 N.

Example 23

32 mg Hydromorphone Formulation

TABLE 23

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 40.71 |
| lactose monohydrate | 23.79 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 161 N.

Example 24

32 mg Hydromorphone Formulation

TABLE 24

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 40.00 |
| ethylcellulose | 40.00 |
| Compritol (glycerol behenate) | 20.00 |
| Dosage Form | |
| coated granules | 45.98 |
| lactose monohydrate | 18.52 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 60% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The blended mixture was then compressed in a rotary tablet press to form tablets. The capsule-shaped tablets (0.625×0.275 in) weighed 600 mg and had an average hardness of 135 N.

Example 25

32 mg Hydromorphone Formulation

TABLE 25

| Materials | % w/w |
|---|---|
| Uncoated Granules | |
| hydromorphone HCl | 27.00 |
| hydroxypropylmethylcellulose (K100M) | 20.00 |
| ethylcellulose | 42.95 |
| Compritol (glycerol behenate) | 10.00 |
| butylated hydroxyanisole | 0.05 |
| Coated Granules | |
| uncoated granules | 60.00 |
| ethylcellulose | 26.67 |
| Compritol (glycerol behenate) | 13.33 |
| Dosage Form | |
| coated granules | 41.03 |
| lactose monohydrate | 23.47 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 40% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 500 mg and had an average hardness of 85 N.

Example 26

12 mg Hydromorphone Formulation

TABLE 26

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 15.27 |
| lactose monohydrate | 49.23 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 600 mg and had an average hardness of 210 N.

Example 27

12 mg Hydromorphone Formulation

TABLE 27

| Materials | % w/w |
|---|---|
| Uncoated Granules | |
| hydromorphone HCl | 27.00 |
| hydroxypropylmethylcellulose | 52.28 |

TABLE 27-continued

| Materials | % w/w |
|---|---|
| (K100M) | |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 15.27 |
| lactose monohydrate | 24.23 |
| microcrystalline cellulose (Avicel PH-102) | 25.00 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose, hydroxypropylmethylcellulose, and Avicel PH-102 in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625×0.275 in) weighed 600 mg and had an average hardness of 260 N.

Example 28

12 mg Hydromorphone Formulation

TABLE 28

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 15.27 |
| lactose monohydrate | 24.23 |
| ethylcellulose T10 | 25.00 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625×0.275 in) weighed 600 mg and had an average hardness of 256 N.

Example 29

32 mg Hydromorphone Formulation

TABLE 29

| Materials | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 40.00 |
| ethylcellulose | 40.00 |
| Compritol (glycerol behenate) | 20.00 |
| Dosage Form | |
| coated granules | 49.38 |
| lactose monohydrate | 15.12 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 60% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 600 mg and had an average hardness of 106 N.

Example 30

32 mg Hydromorphone Formulation

TABLE 30

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 39.80 |
| lactose monohydrate | 24.70 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 600 mg and had an average hardness of 138 N.

Example 31

32 mg Hydromorphone Formulation

TABLE 31

| Material | % w/w |
|---|---|
| Uncoated Granules | |
| hydromorphone HCl | 27.00 |
| hydroxypropylmethylcellulose (K100M) | 20.00 |
| ethylcellulose | 42.95 |
| Compritol (glycerol behenate) | 10.00 |
| butylated hydroxyanisole | 0.05 |
| Coated Granules | |
| uncoated granules | 60.00 |
| ethylcellulose | 26.33 |
| Compritol (glycerol behenate) | 13.67 |
| Dosage Form | |
| coated granules | 33.54 |
| lactose monohydrate | 30.96 |
| hydroxypropylmethylcellulose (K100 M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 40% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 600 mg and had an average hardness of 130 N.

Example 32

12 mg Hydromorphone Formulation

TABLE 32

| Material | % w/w |
|---|---|
| Uncoated Granules | |
| hydromorphone HCl | 27.00 |
| hydroxypropylmethylcellulose (K100M) | 52.28 |

TABLE 32-continued

| Material | % w/w |
|---|---|
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 14.93 |
| lactose monohydrate | 24.57 |
| hydroxypropylmethylcellulose (K100 M) | 35.00 |
| microcrystalline cellulose | 25.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 600 mg and had an average hardness of 293 N.

Example 33

12 mg Hydromorphone Formulation

TABLE 33

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 55.00 |
| ethylcellulose | 30.00 |
| Compritol (glycerol behenate) | 15.00 |
| Dosage Form | |
| coated granules | 14.39 |
| lactose monohydrate | 24.90 |
| microcrystalline cellulose (Avicel PH 113) | 25.06 |
| hydroxypropylmethylcellulose (K100M) | 35.05 |

TABLE 33-continued

| Material | % w/w |
|---|---|
| Color | 0.10 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/Compritol mixture to provide a coat of 45% by weight of the coated granules. The color and Avicel PH 113 were blended in a V-blender for 15 minutes and milled. The milled blend was blended with coated granules, lactose and hydroxypropylmethylcellulose for 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.5000× 0.3125 in) weighed 600 mg and had an average hardness of 249 N.

Example 34

16 mg Hydromorphone Formulation

TABLE 34

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 55.00 |
| ethylcellulose | 30.00 |
| Compritol (glycerol behenate) | 15.00 |
| Dosage Form | |
| coated granules | 17.10 |
| lactose monohydrate | 27.30 |
| microcrystalline cellulose (Avicel PH 113) | 19.97 |
| hydroxypropylmethylcellulose (K100M) | 35.03 |
| Color | 0.10 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/Compritol mixture to provide a coat of 45% by weight of the coated granules. The color and Avicel PH 113 were blended in a V-blender for 15 minutes and milled. The milled blend was blended with coated granules, lactose and hydroxypropylmethylcellulose for 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.5000× 0.3125 in) weighed 600 mg and had an average hardness of 206 N.

Example 35

24 mg Hydromorphone Formulation

TABLE 35

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 55.00 |
| ethylcellulose | 30.00 |
| Compritol (glycerol behenate) | 15.00 |
| Dosage Form | |
| coated granules | 25.64 |
| lactose monohydrate | 28.76 |
| microcrystalline cellulose (Avicel PH 113) | 10.00 |
| hydroxypropylmethylcellulose (K100M) | 35.00 |
| Color | 0.10 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/Compritol mixture to provide a coat of 45% by weight of the coated granules. The color and Avicel PH 113 were blended in a V-blender for 15 minutes and milled. The milled blend was blended with coated granules, lactose and hydroxypropylmethylcellulose for 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.5000× 0.3125 in) weighed 600 mg and had an average hardness of 171 N.

Example 36

12 mg Hydromorphone Formulation

TABLE 36

| Material | % w/w |
|---|---|
| Uncoated Granules | |
| hydromorphone HCl | 27.00 |
| hydroxypropylmethylcellulose (K100M) | 52.28 |
| ethylcellulose | 20.67 |
| butylated hydroxyanisole | 0.05 |
| Coated Granules | |
| uncoated granules | 50.00 |
| ethylcellulose | 33.33 |
| Compritol (glycerol behenate) | 16.67 |
| Dosage Form | |
| coated granules | 14.93 |
| lactose monohydrate | 24.47 |
| hydroxypropylmethylcellulose (K100 M) | 35.00 |
| microcrystalline cellulose | 25.00 |
| Red iron oxide | 0.10 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. The red iron oxide and Avicel PH 113 were blended in a V-blender for 15 minutes and milled. The milled blend was blended with coated granules, lactose and hydroxypropylmethylcellulose for 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625×0.275 in) weighed 600 mg and had an average hardness of nearly 150 N.

Example 37

32 mg Hydromorphone Formulation

TABLE 37

| Material | % w/w |
|---|---|
| *Uncoated Granules* | |
| hydromorphone HCl | 27.00 |
| hydroxypropylmethylcellulose (K100M) | 52.28 |
| ethylcellulose | 20.67 |
| butylated hydroxyanisole | 0.05 |
| *Coated Granules* | |
| uncoated granules | 50.00 |
| ethylcellulose | 33.33 |
| Compritol (glycerol behenate) | 16.67 |
| *Dosage Form* | |
| coated granules | 39.80 |
| lactose monohydrate | 24.70 |
| hydroxypropylmethylcellulose (K100M) | 35.00 |
| magnesium stearate | 0.50 |

Granules were manufactured in a high shear granulator where hydromorphone HCl, hydroxypropylmethylcellulose and a portion of the ethylcellulose were dry mixed for 2 minutes. Then, an ethanolic solution of the remaining ethylcellulose and butylated hydroxyanisole was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% alcoholic suspension of a 2:1 ethylcellulose/compritol mixture to provide a coat of 50% by weight of the coated granules. Coated granules were mixed with lactose and hydroxypropylmethylcellulose in a V-blender for a period of about 30 minutes. Magnesium stearate was added and the mixture blended for an additional 5 minutes. The amount of coated granules charged into the tablet is based on the actual coated granule content of hydromorphone, it is not based on the theoretical content. The blended mixture was then compressed in a rotary tablet press to form tablets. The capsule-shaped tablets (0.625× 0.275 in) weighed 600 mg and had an average hardness of nearly 45 N.

Example 38

Dissolution Rates and Tamper Resistance

Dissolution in 0.1N HCl, 0.1N HCl and 40% v/v alcohol, and simulated oral tampering of various formulations disclosed herein were tested. As shown in Table 38, tablets were tested using the USP dissolution apparatus number 2 using 500 mL of 0.1 N HCl (normal dissolution) or 40% ethanolic solution (dose dumping dissolution) as the dissolution medium. Unless otherwise specified, aliquots were removed after 60, 120, 240, 480, 720, 960, 1200, and 1440 minutes of stirring in the normal dissolution test and after 15, 30, 45, 60, 120, 180, 240, and 360 minutes for the dose dumping dissolution. Samples were analyzed for hydromorphone using HPLC.

Simulated oral tampering testing was conducted by crushing the tablets using ceramic mortars and pestles. A tablet is placed in a ceramic mortar (13 cm outer diameter). A pestle is used to apply force vertically downward onto the tablet until it breaks. The broken tablet is further crushed using a 360° circular motion with downward force applied throughout. The circular crushing motion is repeated eleven times (twelve strokes total). The resulting powder is transferred to a dissolution vessel for in vitro drug release. The in vitro release profile of the crushed tablet samples is obtained in 500 mL of 0.1 N HCl dissolution medium. The samples are agitated at 50 rpm with USP apparatus 2 (paddles) at 37° C. These are the same in vitro conditions as those employed in the in vitro dissolution test described above. Unless otherwise specified, aliquots are removed after 15, 30, 45, 60, and 120 minutes of stirring and are analyzed for hydromorphone using HPLC.

Results of the above experiments are detailed in Table 38. Dissolution samples were graded on a pass/fail basis based on samples collected at 16 hours and 20 hours. Samples received a passing grade if the percent of hydromorphone released was <85% and <90%, respectively. Tablets were considered to be alcohol-resistant if the percent of hydromorphone released after 2 hours in 0.1N HCl/40% v/v alcohol was no more than 10 percentage points greater than the percent of hydromorphone released after 2 hours from a solution of 0.1N HCl in the absence of alcohol. Tablets which exhibited a release of hydromorphone 30 minutes after simulated oral tampering that was less than about 50 percent were given a passing grade.

TABLE 38

| Example No. | % hydromorphone released after 16 hours <85% | % hydromorphone released after 20 hours <90% | % hydromorphone released 30 minutes following crushing <50% | Difference in % hydromorphone released between normal dissolution and dose dumping dissolution ≤10% |
|---|---|---|---|---|
| 1 | P | P | P | F |
| 2 | P | P | P | F |
| 3 | P | P | P | F |
| 4 | P | P | F | P |
| 5 | P | P | P | P |
| 6 | P | P | P | P |
| 7 | P | P | — | P |
| 8 | P | P | — | P |
| 9 | P | P | P | P |
| 10 | P | P | P | P |
| 11 | P | P | P | F |
| 12 | P | P | P | P |

TABLE 38-continued

| Example No. | % hydromorphone released after 16 hours <85% | % hydromorphone released after 20 hours <90% | % hydromorphone released 30 minutes following crushing <50% | Difference in % hydromorphone released between normal dissolution and dose dumping dissolution ≤10% |
|---|---|---|---|---|
| 13 | P | P | P | P |
| 14 | P | P | P | P |
| 15 | P | P | P | P |
| 16 | P | P | P | P |
| 17 | P | P | P | P |
| 18 | F | F | — | P |
| 19 | F | F | — | P |
| 20 | F | F | — | P |
| 21 | F | F | — | P |
| 22 | P | F | — | P |
| 23 | F | F | P | P |
| 24 | P | F | P | P |
| 25 | P | F | P | P |
| 26 | F | F | P | P |
| 27 | F | F | P | P |
| 28 | F | F | P | P |
| 29 | P | P | P | P |
| 30 | P | P | P | P |
| 31 | P | P | P | F |
| 32 | F | F | P | P |

— indicates that the tablet was not tested

Example 39

PK Study

Three hydromorphone HCl extended-release tablet formulations, Treatments A (40% coat), B (50% coat), and C (60% coat), and one commercially available immediate-release hydromorphone HCl formulation (Treatment D; 4×8 mg doses) were utilized in this study. Subjects (n=40) were randomly assigned to 1 of 4 treatment sequences: ABCD, BCDA, CDAB, or DABC. The four doses of the immediate-release product were separated by approximately 6 hours.

Hydromorphone was administered to the subjects under fasting conditions. Subjects were to receive each treatment during the study, with a minimum 5-day washout between dosing periods. Subjects also received one 50-mg tablet of naltrexone for blockade of opioid effects every 12 hours starting approximately 15 hours before and continuing until approximately 33 hours after each hydromorphone administration. During each treatment period, venous blood samples (~3 mL each) were collected from each subject by venipuncture or indwelling catheter for determination of plasma concentrations of hydromorphone. Samples were collected immediately before and 15, 30, and 45 minutes, and 1, 1.25, 1.5, 1.75, 2, 2.25, 2.5, 3, 3.5, 4, 5, 6, 8, 10, 12, 18, 24, 30, 36, 48, 60, and 72 hours after administration of Treatments A, B, and C. For Treatment D, samples were collected immediately before and 15, 30, and 45 minutes, and 1, 1.25, 1.5, 1.75, 2, 2.25, 2.5, 3, 3.5, 4, 5, 6, 12, 18, 18.25, 18.5, 18.75, 19, 19.25, 19.5, 19.75, 20, 20.25, 20.5, 21, 21.5, 22, 23, 24, 30, 36, 48, 60, and 72 hours after the initial drug administration.

Concentrations of hydromorphone were determined in human plasma samples using a validated high-performance liquid chromatography method with tandem mass spectrometric detection (LC-MS/MS).

There were 26 male and 13 female healthy volunteers enrolled in the study who received at least 1 of the treatments. The ages of the subjects ranged from 19 to 43 years, with a mean of 28 years. The heights and weights of the subjects ranged from 151.5 to 190.5 cm (mean, 170.6 cm) and from 56.4 to 97.7 kg (mean, 73.6 kg), respectively. The body mass indices of the subjects ranged from 20.8 to 29.7 kg/m2 (mean, 25.3 kg/m2). To be included in the pharmacokinetic analysis set, a subject must have had completed all four treatment periods; 33 of the subjects enrolled met this criterion.

Results of the study are shown in FIG. 1 and Table 39, below.

TABLE 39

| Parameter | Hydromorphone ER (40% coat) | Hydromorphone ER (50% coat) | Hydromorphone ER (60% coat) | Hydromorphone IR |
|---|---|---|---|---|
| $C_{max}$ (ng/mL) | 3.035 (0.980) | 3.154 (0.891) | 2.881 (0.868) | 6.192 (2.053) |
| $t_{max}$ (hr)$^a$ | 11.9 [5.0-36.0] | 10.0 [1.75-36.0] | 11.9 [2.0-36.0] | 18.5 [0.25-22.0] |
| $t_{max}^*$ (hr)$^a$ | — | — | — | 0.75 [0.25-4.0] |
| $AUC_{0-24}$ (ng?hr/mL) | 43.75 (12.31) | 48.61 (12.63) | 42.95 (12.11) | — |
| $AUC_{0-72}$ (ng?hr/mL) | 85.02 (24.65) | 84.02 (23.82) | 82.91 (25.71) | — |
| $AUC_{0-t}$ (ng?hr/mL) | 85.00 (24.69) | 83.84 (23.99) | 82.69 (25.94) | 82.52 (18.95) |
| $AUC_{0-?}$ (ng?hr/mL) | 88.85 (25.74) | 87.15 (25.44) | 87.17 (26.15) | 85.09 (20.11) |
| $AUC_{0-6}$ (ng?hr/mL) | — | — | — | 8.34 (2.34) |
| $AUC_{18-24}$ (ng?hr/mL) | — | — | — | 16.70 (3.95) |

TABLE 39-continued

| Parameter | Hydromorphone ER (40% coat) | Hydromorphone ER (50% coat) | Hydromorphone ER (60% coat) | Hydromorphone IR |
|---|---|---|---|---|
| $t_{1/2}$ (hr)[b] | 13.2 (5.2) [11.9] | 12.4 (3.8) [11.4] | 14.4 (6.5) [12.4] | 12.3 (3.7) [11.4] |
| $\lambda_z$ (hr$^{-1}$) | 0.0584 (0.0172) | 0.0608 (0.0185) | 0.0561 (0.0202) | 0.0609 (0.0161) |
| AUC Extrap. (%) | 4.3 (3.9) | 3.7 (2.9) | 5.4 (5.2) | 2.9 (2.1) |

ER: extended release;
IR: immediate release;
[a]median [range];
[b]arithmetic mean (SD) [harmonic mean]
$t_{max}$*: $t_{max}$ relative to most recent dose

Example 40

Effects of Food on Formulation w/o Viscosity Modifier

Using a process similar to that described in Example 14 from publication US2008/0069891, which is herein incorporated by reference in its entirety, granules were formed by dry mixing only 53% of EC with other ingredients, the following formulation was prepared:

TABLE 40

| Ingredient | Amount (% w/w) |
|---|---|
| Oxycodone HCl | 46.1 |
| Hydroxypropyl methylcellulose (HPMC) | 36.9 |
| Ethylcellulose | 17.0 |
| Total | 100.00 |

TABLE 41

| Ingredient | Amount (% w/w) |
|---|---|
| Oxycodone granules (oxycodone HCl, HPMC, ethylcellulose) | 52.5 |
| Ethylcellulose | 31.7 |
| Magnesium stearate | 15.8 |
| Total | 100.00 |

Using a process similar to that described in Example 37, the following formulation was used to prepare tablets:

TABLE 42

| Component | Amount (% w/w) | Amount (mg) |
|---|---|---|
| Oxycodone coated granules | 38.89* | 330.6 |
| Lactose Monohydrate (fast Flo) | 51.11 | 434.4 |
| COMPRITOL (glyceryl behenate) | 10.00 | 85.0 |
| Total | 100.00 | 850.0 mg |

While COMPRITOL is always kept at 10% of the total weight of the dosage form (tablet), any change in the actual assay amount, from theoretical values, is accounted for by changing the amount of lactose and coated granules to maintain the amount of Oxycodone HCl at 80 mg per tablet. The average tablet weight is 850 mg, and has an average hardness of between 140 and 155 N. The tablet dimensions are 0.3125"×0.5625".

The above described tablets were then used in a Phase 1, single-center, randomized, open-label, 3-period study to assess the effect of food on the single-dose pharmacokinetics of 80-mg oxycodone hydrochloride extended release tablets and to characterize the single- and multiple-dose pharmacokinetics of 80-mg oxycodone hydrochloride extended release tablets in healthy subjects.

Subjects were randomly assigned to 1 of 2 treatment sequences: ABC or BAC, whereby A was a single dose of the 80-mg oxycodone hydrochloride extended release tablet administered with the subject in a fasted state, B was a single dose of the 80-mg oxycodone hydrochloride extended release tablet administered with the subject in a fed state, and C was one 80-mg oxycodone hydrochloride extended release administered twice daily (bid) for 4.5 days (data from treatment group C not shown).

The study consisted of a screening visit (visit 1) within 21 days before the 1st dose of study drug, followed by 2 open-label single-dose administration periods (periods 1 and 2, visits 2 and 3); 1 open-label, 4.5-day, multiple-dose administration period (period 3, included in visit 3); and a follow-up visit (visit 4). There was a minimum 5-day washout between administration of study drug in periods 1 and 2. Administration period 3 began immediately after collection of the 48-hour pharmacokinetic sample in administration period 2.

Subjects received all 3 treatments during the study. Subjects received 50 mg of naltrexone with 240 mL of water to block opioid receptors and minimize opioid-related adverse events approximately 15 and 3 hours before administration and approximately 9 and 21 hours after administration in periods 1 and 2. Additionally, during administration period 2, subjects received naltrexone approximately 33 and 45 hours after study drug administration (in preparation for study drug administration in period 3).

During administration period 3, subjects received naltrexone every 12 hours through 21 hours after the last study drug administration on day 5.

Subjects were required to fast (no food or beverages) overnight beginning at approximately 2100 hours on the evening prior to study drug administration in periods 1 and 2. Subjects randomly assigned to Treatment A continued to fast for a minimum of 4 hours after study drug administration. Subjects randomly assigned to Treatment B fasted until approximately 30 minutes prior to study drug administration, at which time they were provided a standard high-fat breakfast, which must have been consumed in its entirety prior to dosing. Subjects receiving Treatment B were then required to remain fasting until a minimum of 4 hours after study drug administration. All subjects (irrespective of randomized treatment) were permitted to have nonmineral water up to 1 hour before and starting 1 hour after each study drug administration.

During the administration period for Treatments A and B, blood samples (3 mL) were collected by venipuncture or indwelling catheter. Samples were collected immediately (within approximately 5 minutes) before each study drug administration and 15, 30, and 45 minutes and 1, 1.5, 2, 2.5, 3, 3.5, 4, 5, 6, 7, 8, 10, 12, 16, 24, 36, and 48 hours after each study drug administration.

In this study, 30 subjects were enrolled and randomly assigned to a treatment sequence; all 30 subjects received at least 1 dose of study drug; 25 (83%) subjects were evaluable for pharmacokinetic analysis; and 23 (77%) subjects completed the study.

TABLE 43

Mean (+/−SD) Pharmacokinetic Parameters for Oxycodone in Healthy Volunteers of 80-mg Oxycodone ER Tablets under Fasted or Fed Conditions

| Parameter | Oxycodone ER (Fasted) | Oxycodone ER (Fed) |
|---|---|---|
| Cmax (ng/mL) | 81.9 ± 22.23 | 135.1 ± 20.47 |
| tmax (hr)a | 8.0 (3.0-12.0) | 5.0 (4.0-10.0) |
| AUC0-12 (ng · hr/mL) | 637.8 ± 150.29 | 870.8 ± 136.17 |
| AUC0-t (ng · hr/mL) | 1140.6 ± 233.66 | 1215.6 ± 253.02 |
| AUC0-∞ (ng · hr/mL) | 1145.8 ± 234.70 | 1218.8 ± 253.97 |
| t½ (hr)b | 5.4 ± 0.58 | 5.3 ± 0.90 |
| λz (hr−1) | 0.13 ± 0.013 | 0.13 ± 0.023 |
| AUC Extrap. (%) | 0.46 ± 0.325 | 0.26 ± 0.185 |

ER: Extended release;
amedian [range];
bmean ± standard deviation [harmonic mean]

breakfast 30 minutes predose), and with varying amounts of alcohol in a fasted state. Subjects (n=40) were randomly assigned to 1 of the following 5 treatment sequences: ABCDE, BCDEA, CDEAB, DEABC, or EABCD, whereby A was the tablet administered under fasted conditions with 240 mL water, B was the tablet administered under fed conditions with 240 mL water, and C, D, and E included administration of the tablet under fasted conditions with 240 mL of 4%, 20%, or 40% ethanol, respectively.

Subjects received each treatment during the study, with a minimum 5-day washout between dosing periods. Subjects also received one 50-mg tablet of naltrexone HCl for blockade of opioid effects approximately 15 hours and 3 hours before each hydromorphone administration and approximately 9 hours and 21 hours after each hydromorphone administration. During each treatment period, venous blood samples (~3 mL each) were collected from each subject by venipuncture or indwelling catheter for determination of plasma concentrations of hydromorphone. Samples were collected immediately before each hydromorphone administration and 15, 30, and 45 minutes and 1, 1.25, 1.5, 1.75, 2, 2.25, 2.5, 3, 3.5, 4, 5, 6, 8, 10, 12, 18, 24, 30, 36, 48, 60, and 72 hours after each administration.

Concentrations of hydromorphone were determined in human plasma samples using a validated high-performance liquid chromatography method with tandem mass spectrometric detection (LC-MS/MS). Results are shown in FIGS. 2-6 and Table 40.

TABLE 44

Mean (+/−SD) Pharmacokinetic Parameters for Hydromorphone in Healthy Volunteers Administered Single Doses of 12 mg Hydromorphone ER Tablets under Fasted or Fed Conditions or with Ethanol

| Parameter | Hydromorphone ER (Fasted) | Hydromorphone ER (Fed) | Hydromorphone ER (4% Ethanol) | Hydromorphone ER (20% Ethanol) | Hydromorphone ER (40% Ethanol) |
|---|---|---|---|---|---|
| Cmax (ng/mL) | 1.194 ± 0.387 | 1.708 ± 0.563 | 1.270 ± 0.411 | 1.205 ± 0.314 | 1.442 ± 0.614 |
| tmax (hr)a | 5.0 [1.75-12.1] | 5.0 [2.0-12.0] | 12.0 [1.5-12.0] | 12.0 [1.75-12.0] | 2.0 [1.5-12.0] |
| AUC0-24 (ng · hr/mL) | 17.9 ± 6.1 | 22.5 ± 6.6 | 18.2 ± 5.7 | 17.5 ± 4.8 | 17.6 ± 7.7 |
| AUC0-72 (ng · hr/mL) | 29.1 ± 10.1 | 31.9 ± 9.7 | 28.1 ± 9.6 | 27.7 ± 8.7 | 27.6 ± 10.4 |
| AUC0-t (ng · hr/mL) | 28.4 ± 10.3 | 31.3 ± 9.8 | 27.4 ± 9.9 | 27.0 ± 9.0 | 25.9 ± 11.1 |
| AUC0-∞ (ng · hr/mL) | 29.9 ± 10.4 | 32.5 ± 9.9 | 28.9 ± 10.1 | 28.6 ± 8.8 | 28.5 ± 10.8 |
| t½ (hr)b | 11.2 ± 3.1 [10.4] | 10.8 ± 2.9 [10.1] | 12.0 ± 2.6 [11.5] | 12.5 ± 3.0 [11.8] | 11.9 ± 6.4 [9.0] |
| λz (hr−1) | 0.0669 ± 0.0197 | 0.0686 ± 0.0198 | 0.0604 ± 0.0132 | 0.0589 ± 0.0157 | 0.0772 ± 0.0526 |
| AUC Extrap. (%) | 5.5 ± 2.4 | 4.0 ± 2.1 | 5.6 ± 3.3 | 6.1 ± 3.8 | 6.3 ± 4.5 |

ER: Extended release;
amedian [range];
bmean ± standard deviation [harmonic mean]

As seen above in Table 43, the co-administration of food with the described formulation lead to nearly 65% increase in mean $C_{max}$ and shifted the median $T_{max}$ 3.0 hours earlier.

Example 41

Effects of Food and Alcohol on PK Parameters

This was a Phase 1, single-center, randomized, open-label, 5-period crossover study in healthy male and female volunteers to characterize the pharmacokinetics of hydromorphone following administration of a 12-mg hydromorphone HCl extended release prototype (50% coat as described in Example 32 above) with water in a fasted state (i.e. no food from approximately 10 hours predose to 4 hours postdose), with water in a fed state (i.e. standard high-fat The results from Table 44 above indicate that, in fasted patients, no dose dumping was observed at differing levels of alcohol consumption. Thus, another embodiment of the invention provides a method of treating pain comprising administering to a patient who has not eaten for at least about 8 hours (e.g. at least about 10 hours) an effective amount of formulation of the invention, or administering to a patient who has eaten within 10, 8, 6, 4, or 2 hours, an effective amount of formulation.

Example 42

Effect of pH on Dissolution Rates

Figure 7:
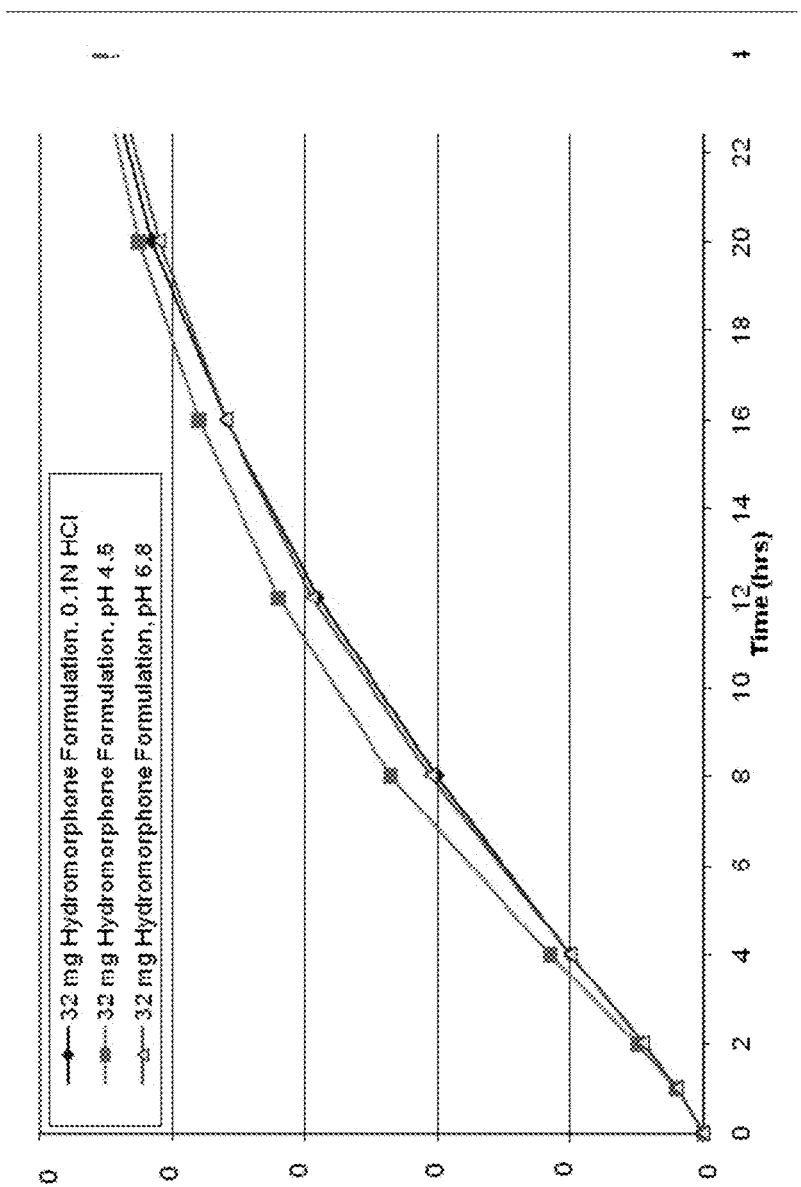
FIG. 7 is a line drawing comparing the % release of hydromorphone from a 32 mg hydromorphone formulation of the invention as a function of time in dissolution media at varying pH.
Figure 8:
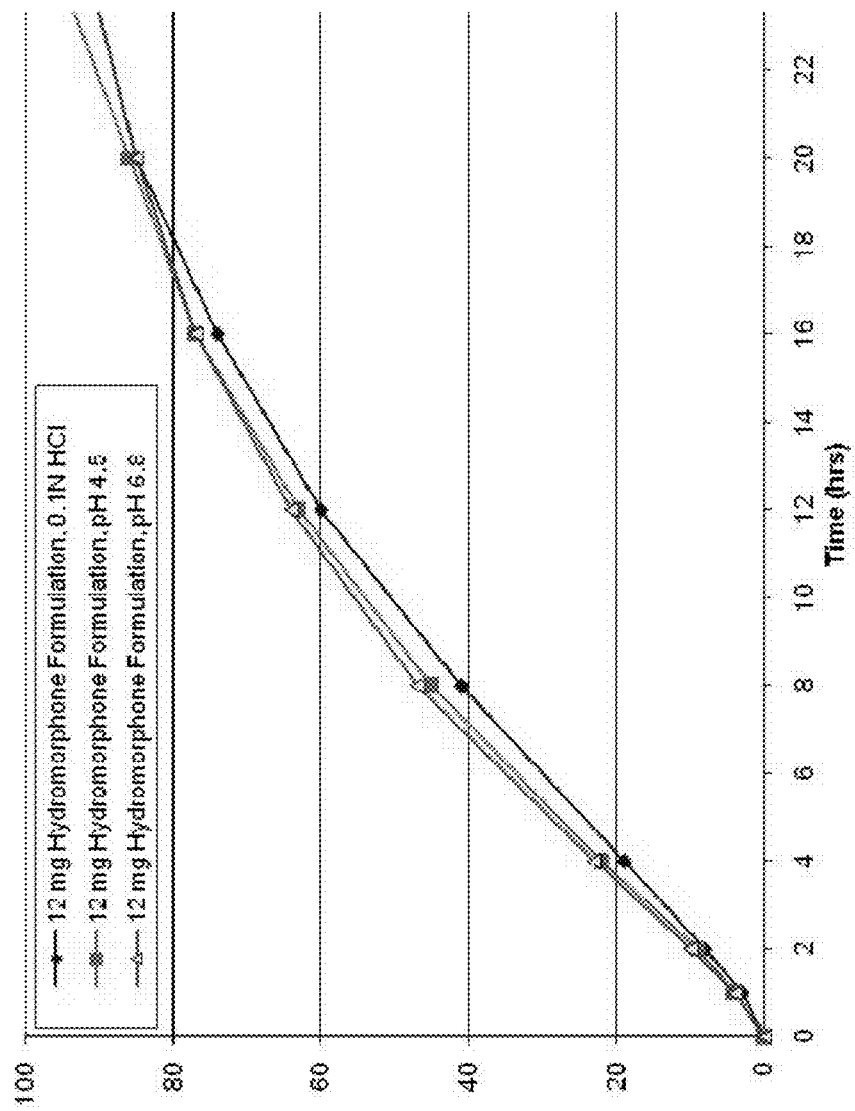
FIG. 8 is a line drawing comparing the % release of hydromorphone from a 12 mg hydromorphone formulation of the invention as a function of time in dissolution media at varying pH.

Dissolution in 0.1N HCl, in dissolution medium at pH 4.5 and in dissolution medium at pH 6.8 of formulations described in Examples 36 and 37 were tested. Tablets were tested using the USP dissolution apparatus number 2 using 500 mL of 0.1 N HCl (normal dissolution), 22 mM sodium acetate trihydrate buffer, adjusted to pH 4.5 with glacial acetic acid, and 50 mM potassium phosphate monobasic buffer, adjusted to pH 6.8 with 1 N sodium hydroxide as the dissolution media. Aliquots were removed after 60, 120, 240, 480, 720, 960, 1200, and 1440 minutes of stirring. Samples were analyzed for hydromorphone using HPLC. Results are shown in FIGS. 7 and 8.

A number of embodiments of the invention have been described. Nevertheless, it will be understood that various modifications may be made without departing from the spirit and scope of the invention. Accordingly, other embodiments are within the scope of the following claims.

What is claimed is:

1. A method of making a stable dosage form containing a single active pharmaceutical ingredient (API), which is hydromorphone, said method comprising:
   granulating an amount of the single API, which is hydromorphone or a salt thereof, a first viscosity modifier and a first strong film former in the presence of a solvent consisting of an organic solvent to form a granule;
   coating the granule with a coating comprising a second strong film former and a fat/wax to form a coated granulate;
   compressing the granulate in a matrix, wherein the matrix comprises a second viscosity modifier;
   wherein the second strong film former comprises ethylcellulose, and the fat wax comprises a glycerol fatty ester.

2. The method according to claim 1, wherein the first viscosity modifier is selected from sodium alginate, hydroxypropylmethylcellulose, hydroxyethylcellulose, hydroxypropylcellulose, methylcellulose, carboxymethylcellulose, sodium carboxymethylcellulose, polyvinylpyrrolidone, crosslinked polyacrylic acid, gelatin, pectins, gums, polyethylene oxides, Konjac flour, carrageenan, xanthan gum, or mixtures thereof.

3. The method according to claim 1, wherein the second viscosity modifier is selected from sodium alginate, hydroxypropylmethylcellulose, hydroxyethylcellulose, hydroxypropylcellulose, methylcellulose, carboxymethylcellulose, sodium carboxymethylcellulose, polyvinylpyrrolidone, crosslinked polyacrylic acid, gelatin, pectins, gums, polyethylene oxides, Konjac flour, carrageenan, xanthan gum, or mixtures thereof.

4. The method according to claim 1, wherein the first viscosity modifier is hydroxypropylmethylcellulose.

5. The method according to claim 1, wherein the second viscosity modifier is hydroxypropylmethylcellulose.

6. The method according to claim 1, wherein the first strong film former is selected from natural and synthetic starches, natural and synthetic celluloses, acrylics, vinylics, resins, methacrylate and shellac.

7. The method according to claim 1, wherein the second strong film former is selected from natural and synthetic starches, natural and synthetic celluloses, acrylics, vinylics, resins, methacrylate and shellac.

8. The method according to claim 1, wherein the first strong film former comprises ethylcellulose.

9. The method according to claim 1, wherein the second viscosity modifier is in an amount of from 30 to 60 percent by weight of the dosage form.

10. The method according to claim 1, wherein the first viscosity modifier and the second viscosity modifier are the same.

11. The method according to claim 1, wherein the first viscosity modifier and the second viscosity modifier are gelling polymers.

12. A tablet containing a single API which is hydromorphone, said tablet comprising:
    a granule comprising an amount of the single API which is hydromorphone or a salt thereof, a first viscosity modifier, a first strong film former and no exogenous water; and a coating substantially surrounding the granule to form a coated granule,
    wherein the coating comprises a second strong film former and a fat/wax; and a matrix comprising a second viscosity modifier,
    wherein the coated granule is compressed in the matrix;
    wherein the tablet is made according to the method of claim 1
    wherein the second strong film former comprises ethylcellulose, and the fat wax comprises a glycerol fatty ester.

* * * * *